(12) United States Patent
Moon et al.

(10) Patent No.: US 11,611,224 B2
(45) Date of Patent: Mar. 21, 2023

(54) ELECTRONIC DEVICE AND CHARGING MODULE SYSTEM COMPRISING SAME

(71) Applicant: Samsung Electronics Co., Ltd., Gyeonggi-do (KR)

(72) Inventors: Jung-Pil Moon, Gyeonggi-do (KR); Yongjin Lee, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 412 days.

(21) Appl. No.: 16/756,537

(22) PCT Filed: Aug. 30, 2018

(86) PCT No.: PCT/KR2018/010067
§ 371 (c)(1),
(2) Date: Apr. 16, 2020

(87) PCT Pub. No.: WO2019/093637
PCT Pub. Date: May 16, 2019

(65) Prior Publication Data
US 2021/0399563 A1  Dec. 23, 2021

(30) Foreign Application Priority Data
Nov. 10, 2017 (KR) .................. 10-2017-0149758

(51) Int. Cl.
*H02J 7/00* (2006.01)
*A61B 5/026* (2006.01)
*A61B 5/00* (2006.01)

(52) U.S. Cl.
CPC .......... *H02J 7/0044* (2013.01); *A61B 5/0261* (2013.01); *A61B 5/681* (2013.01); *H02J 2310/23* (2020.01)

(58) Field of Classification Search
CPC .......... G06K 9/00; A61B 5/0261; A61B 5/681
See application file for complete search history.

(56) References Cited

U.S. PATENT DOCUMENTS 9,295,403 B1    3/2016  Mirov et al.
2012/0206090 A1  8/2012  Hyun-Jun et al.
(Continued)

FOREIGN PATENT DOCUMENTS

JP    2004-064961 A    2/2004
JP    2014-161192 A    9/2014
(Continued)

OTHER PUBLICATIONS

Examination Report dated Jul. 21, 2022.
Decision on Grant dated Dec. 2, 2022.

*Primary Examiner* — Myron Wyche
(74) *Attorney, Agent, or Firm* — Cha & Reiter, LLC

(57) ABSTRACT

An electronic device of a charging module system may include a housing having a first surface facing a first direction and a second surface facing a second direction opposite to the first direction; a display device at least partially is exposed through the first surface to display information to the outside; a biometric sensor disposed to be exposed in at least an area of the second surface and sensing biometric information of a user; a battery disposed between the display device and the biometric sensor; and a plurality of electrodes disposed adjacent to the at least an area of the second surface and formed to be exposed in at least another area of the second surface, in which the plurality of electrodes may surround at least a portion of the biometric sensor, and each of the plurality of electrodes has a notch protruding or recessed at least at one end.

13 Claims, 12 Drawing Sheets

(56) References Cited

U.S. PATENT DOCUMENTS

| | | |
|---|---|---|
| 2016/0056647 A1 | 2/2016 | Choi |
| 2016/0172890 A1 | 6/2016 | Jeong |
| 2016/0192856 A1 | 7/2016 | Lee |
| 2017/0063107 A1 | 3/2017 | Lee et al. |
| 2017/0181702 A1 | 6/2017 | Koh et al. |
| 2018/0248406 A1 | 8/2018 | Bae et al. |
| 2018/0250805 A1 | 9/2018 | Takidis et al. |
| 2019/0038224 A1* | 2/2019 | Zhang ................. A61B 5/6843 |

FOREIGN PATENT DOCUMENTS

| | | | |
|---|---|---|---|
| JP | 2016-189562 A | 11/2016 | |
| KR | 10-2012-0092450 A | 8/2012 | |
| KR | 20120092450 * | 8/2012 | ............... H02J 7/00 |
| KR | 10-2016-0024415 A | 3/2016 | |
| KR | 10-2016-0095535 A | 8/2016 | |
| KR | 10-2016-0142716 A | 12/2016 | |
| KR | 20160142716 * | 12/2016 | ............... G06K 9/00 |
| KR | 10-2017-0025069 A | 3/2017 | |
| KR | 10-2017-0027624 A | 3/2017 | |
| KR | 10-2017-0078386 A | 7/2017 | |
| WO | 2017-017522 A1 | 2/2017 | |

\* cited by examiner

ELECTRONIC DEVICE AND CHARGING MODULE SYSTEM COMPRISING SAME

CROSS-REFERENCE TO RELATED APPLICATION(S)

This application is a National Phase Entry under 35 U.S.C. § 371 of PCT International Application No. PCT/KR2018/010067, which was filed on Aug. 30, 2018, and claims priority to Korean Patent Application No. 10-2017-0149758, which was filed in the Korean Intellectual Property Office on Nov. 10, 2017, the entire contents of each of which are incorporated herein by reference.

BACKGROUND

1. Field

Various embodiments relate to an electronic device and a charging module system having the electronic device and being capable of self-alignment.

2. Description of the Related Art

An electronic device may mean a device that performs specific functions in accordance with programs installed therein, such as an electronic notepad, a mobile multimedia player, a mobile communication terminal, a tablet PC, a video/sound device, a desktop/laptop computer, and an automobile navigation system, including home appliances. For example, these electronic devices can output information stored therein using sound or images. As electronic devices have become highly integrated and high-speed and large-capacity wireless communication has been popularized, recently, it has become possible to integrate various functions into a single electronic device such as a mobile communication terminal. For example, not only a communication function, but also an entertainment function such as a game, a multimedia function such as playback of music/video, a communication and security function for mobile banking, and the function of a schedule manager, an electronic wallet, etc., have come to be integrated into a single electronic device.

Electronic devices that are intended to be carried are generally equipped with a flat panel display and a battery and the types thereof include a bar type, a foldable type, and a slidable type. Recently, with the development of electronic communication technology, electronic devices having small sizes have been developed, and electronic devices that can be worn on a part of a human body such as a wrist or a head have been commercialized.

Led by mobile communication terminals, including wearable electronic devices, electronic devices have been simplified and reduced in weight and thickness and provided with various functions to satisfy the demand of customers. Among various functions provided to such electronic devices, there are various methods of charging a battery, which can be classified into wired charging and wireless charging.

SUMMARY

According to a wireless charging method of methods of charging a battery of an electronic device, a short circuit and breakage of a circuit do not occur, but the charging efficiency may be rapidly changed depending on the positions of the coil of a transmission terminal and the coil of a reception terminal. The charging efficiency of the wireless charging method is lower than that of the wired charging method. According to the wired charging method, a charger and an electronic device are coupled by directly fitting them to each other by using coupling terminal such as a clip or cable, so it may be inconvenient compared to the wireless charging method.

According to various embodiments, it is possible to provide an exact contact point and stable charging by contact, rather than by fitting, through self-alignment of an electronic device of a charging module system, for example, self-alignment between a charging module and a wearable device.

According to various embodiments, a wearable device of electronic devices of a charging module system has a magnetic electrode that can charge a battery and/or measure biometric bio-signal, thereby being able to reduce a mounting space of the device.

According to various embodiments, a plurality of electrodes of a wearable device of electronic devices of a charging module system has notch structures protruding or recessed at some areas, whereby it is possible to electrically couple the wearable device to a charging module in various directions.

An electronic device according to various embodiments may include: a housing having a first surface facing a first direction and a second surface facing a second direction opposite to the first direction; a display device at least partially exposed through the first surface to display information to the outside; a biometric sensor disposed to be exposed in at least an area of the second surface and sensing biometric information of a user; a battery disposed between the display device and the biometric sensor; and a plurality of electrodes disposed adjacent to the at least an area of the second surface and formed to be exposed in at least another area of the second surface, in which the plurality of electrodes may surround at least a portion of the biometric sensor and each of the plurality of electrodes may have a notch protruding or recessed at least at one end.

An electronic device according to various embodiments may include: a housing having a seat forming contact points with an external electronic device; at least one magnet disposed in the housing to face the seat; and a plurality of charging electrodes formed to be exposed to the seat from the housing and forming contact points with the external electronic device, in which the electrodes include a pair of first charging electrodes having a positive (+) pole and a negative (−) pole and another pair of second charging electrodes having a positive (+) pole and a negative (−) pole and disposed in parallel with a virtual line including the pair of first charging electrodes.

A charging module system according to various embodiments includes a first electronic device and a second electronic device charging a battery of the first electronic device, in which the first electronic device includes: a first housing; a biometric sensor disposed to be exposed on a surface of the first housing and sensing biometric information of a user; the battery disposed in the first housing; and a plurality of electrodes disposed opposite to each other with the biometric sensor therebetween and having an end with a protruding or recessed notch, the second electronic device includes: a second housing having a seat where the first electronic device is seated; at least one magnet disposed in the second housing to face the electrodes of the first electronic device; and a plurality of charging electrodes forming contact points with at least a portion of each of the notches of the electrodes of the first electronic device in the second housing, and the magnets of the second electronic device may have a shape corresponding to the electrodes of the first electronic device such that the surface of the first electronic device is self-aligned with the seat of the second electronic device.

According to various embodiments, it is possible to provide an exact contact point and stable charging, not by fitting, but contact, through self-alignment of an electronic device of a charging module system, for example, a charging module and a wearable device.

According to various embodiments, a wearable device of electronic devices of a charging module system has a magnetic electrode that can charge a battery and/or measure biometric signs, thereby being able to reduce a mounting space of the device.

According to various embodiments, a magnet is disposed in a charging module of an electronic device of a charging module system, whereby it is possible to provide magnetic coupling to a wearable device. Further, charging electrodes are disposed around the magnet, whereby it is possible to provide electrical coupling to electrodes of the wearable device.

According to various embodiments, a plurality of electrodes of a wearable device of electronic devices of a charging module system has notch structures protruding or recessed at some areas, whereby it is possible to electrically couple the wearable device to a charging module in various directions.

DETAILED DESCRIPTION

Figure 1:
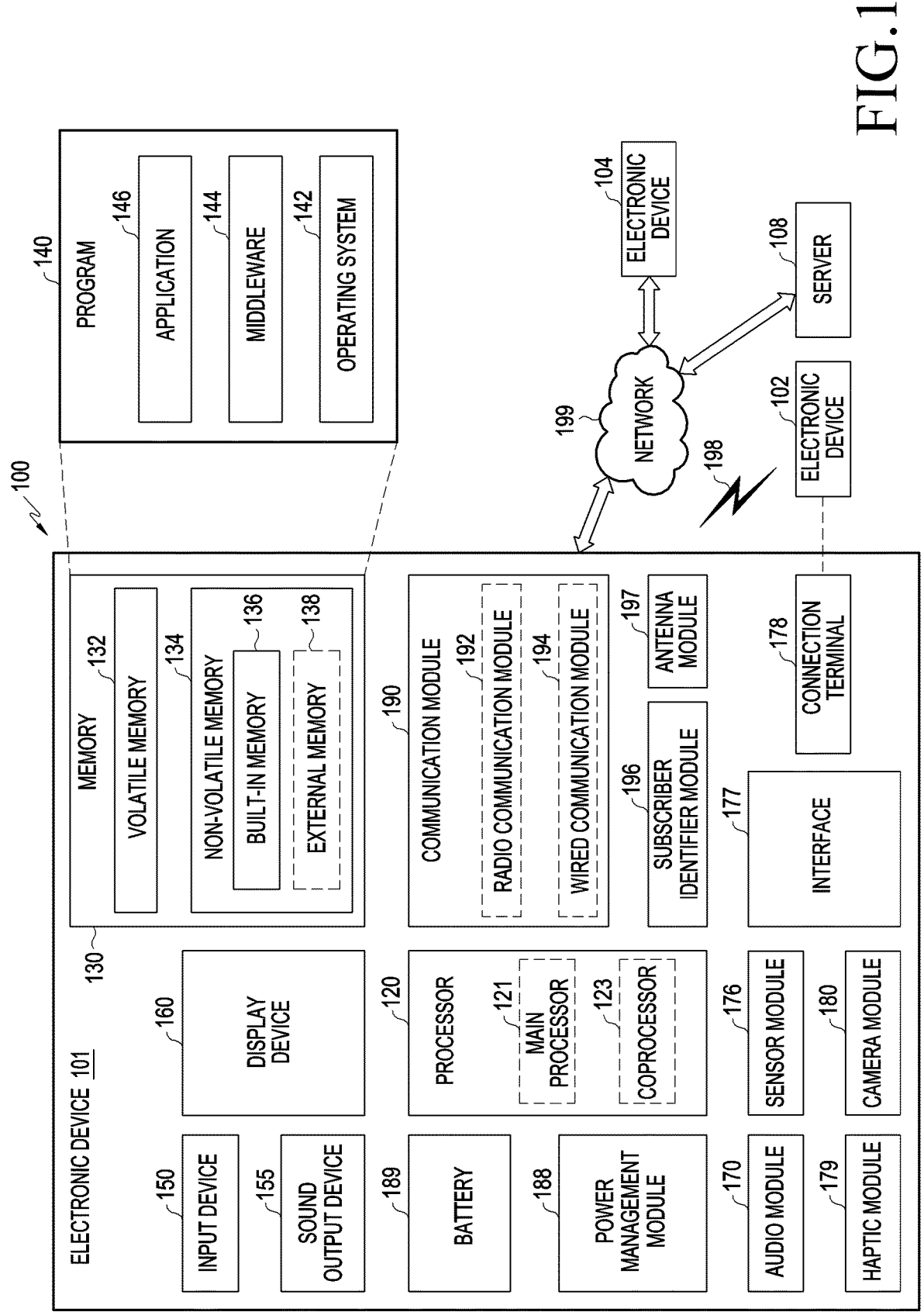
FIG. 1 is a block diagram showing an electronic device in a network environment 100 according to various embodiments.

An electronic device according to various embodiments disclosed herein may be various types of devices. The electronic device may, for example, include at least one of a portable communication device (e.g., smartphone) a computer device, a portable multimedia device, a portable medical device, a camera, a wearable device, and a home appliance. The electronic device according to one embodiment is not limited to the above described devices.

The embodiments and the terms used therein are not intended to limit the technology disclosed herein to specific forms, and should be understood to include various modifications, equivalents, and/or alternatives to the corresponding embodiments. In describing the drawings, similar reference numerals may be used to designate similar constituent elements. A singular expression may include a plural expression unless they are definitely different in a context. The terms "A or B", "one or more of A and/or B", "A, B, or C", or "one or more of A, B and/or C" may include all possible combinations of them. The expression "a first", "a second", "the first", or "the second" used in various embodiments may modify various components regardless of the order and/or the importance but does not limit the corresponding components. When an element (e.g., first element) is referred to as being "(functionally or communicatively) connected," or "directly coupled" to another element (second element), the element may be connected directly to the another element or connected to the another element through yet another element (e.g., third element).

The term "module" as used herein may include a unit consisting of hardware, software, or firmware, and may, for example, be used interchangeably with the term "logic", "logical block", "component", "circuit", or the like. The "module" may be an integrated component, or a minimum unit for performing one or more functions or a part thereof. For example, a module may be an Application-Specific Integrated Circuit (ASIC).

Various embodiments disclosed herein may be implemented by software (e.g., program 140) including an instruction stored in machine-readable storage media (e.g., internal memory 136 or external memory 138). The machine is a device that calls the stored instruction from the storage media and can operate according to the called instruction, and may include an electronic device (e.g., electronic device 101) according to the disclosed embodiments. The instruction, when executed by a processor (e.g., processor 120), may cause the processor to directly execute a function corresponding to the instruction or cause other elements to execute the function under the control of the processor. The instruction may include a code that is generated or executed by a compiler or interpreter. The machine-readable storage media may be provided in the form of non-transitory storage media. Here, the term "non-transitory" means only that the storage media is tangible without including a signal, irrespective of whether data is semi-permanently or transitorily stored in the storage media.

A method according to various embodiments disclosed herein may be included in a computer program product. The computer program product may be traded between a seller and a purchaser as an item. The computer program product may be distributed in the type of a device-readable storage medium (e.g., a Compact Disc Read Only Memory (CD-ROM) or through an application store (e.g., Play Store™) on the web. When the computer program product is distributed on the web, at least a portion of the computer program product may be at least temporarily stored or created in a storage medium such as the memory of the server of the manufacturer, the server of an application store, or a relay server.

Components (e.g., a module or a program) according to various embodiments may be single units or may be composed of various elements, and some of corresponding sub-components may be omitted or other sub-components may be further included in various embodiments. Generally or additionally, some components (e.g., a module or a program) may be integrated in a single unit and perform similarly or in the same way the functions of the components before they are integrated. Operations performed by a module, a programming module, or other elements according to various embodiments may be executed sequentially, in parallel, repeatedly, or in a heuristic manner. At least some operations may be executed according to another sequence, may be omitted, or may further include other operations. Hereinafter, an electronic device according to various embodiments will be described with reference to the accompanying drawings. In the present disclosure, the term "user" may indicate a person using an electronic device or a device (e.g., an artificial intelligence electronic device) using an electronic device.

FIG. 1 is a block diagram of an electronic device 101 in a network environment 100 according to various embodiments. Referring to FIG. 1, the electronic device 101 in the network environment 100 can communicate with an electronic device 102 through a first network 198 (e.g. near field communication) or can communicate with an electronic device 104 or a server 108 through a second network 199 (e.g., long distance wireless communication). According to an embodiment, the electronic device 101 can communicate with the electronic device 104 through the server 108. According to an embodiment, the electronic device 101 may include a processor 120, a memory 130, an input device 150, a sound output device 155, a display device 160, an audio module 170, a sensor module 176, an interface 177, a haptic module 179, a camera module 180, an power management module 188, a battery 189, a communication module 190, a subscriber identifier module 196, and an antenna module 197. In an embodiment, in the electronic device 101, at least one (e.g., the display device 160 or the camera module 180) of the components may be removed or another component may be added. In an embodiment, for example, some components may be integrated such as the sensor module 176 (e.g., a fingerprint sensor, an iris sensor, or an illumination sensor) embedded in the display device 160 (e.g., a display).

The processor 120, for example, can control at least one component (e.g., a hardware or software component) connected to the processor 120 of the electronic device 101 by executing software (e.g., a program 140) and can process and calculate various data. The processor 120 can load and process commands or data received from another component (e.g., the sensor module 176 or the communication module 190) in a volatile memory 132, and can store the resultant data in a nonvolatile memory 134. According to an embodiment, the processor 120 may include a main processor 121 (e.g., a central processing unit or an application processor) and a coprocessor 123 (e.g., a graphic processor, an image signal processor, a sensor hub processor, or a communication processor) that is operated independently from the main processor and, additionally or alternatively, uses less power than the main processor 121 or is specified for predetermined functions. The coprocessor 123 may be operated separately from the main processor 121 or may be embedded and operated.

In this case, the coprocessor 123 can control at least some of the functions or states related to at least one (e.g., the display device 160, the sensor module 176, or the communication module 190) of the components of the electronic device 101, for example, instead of the main processor 121 when the main processor 121 is in an inactive (e.g., sleep) state or together with the main processor 121 when the main processor 121 is in an active state (e.g., in operation for executing an application). According to an embodiment, the coprocessor 123 (e.g., an image signal processor or a communication processor) may be implemented as a partial component of another functionally related component (e.g., the camera module 180 or the communication module 190). The memory 130 can store various data, for example, software (e.g., the program 140) that is used by at least one component (e.g., the processor 120 or the sensor module 176) of the electronic device 101, and can input data or output data for commands related to the software. The memory 130 may include a volatile memory 132 and/or a nonvolatile memory 134.

The program 140, which is software stored in the memory 130, for example, may include an operating system 142, middleware 144, or an application 146.

The input device 150, which is a device for receiving commands or data to be used by components (e.g., the processor 120) of the electronic device 101 from the outside (e.g., a user) of the electronic device 101, may include, for example, a microphone, a mouse, or a keyboard.

The sound output device 155, which is a device for outputting sound signals to the outside of the electronic device 101, for example, may include a speaker that is used for common purposes such as playing of multimedia or recorded sounds, and a receiver that is used only for receiving a telephone call. According to an embodiment, the receiver may be formed integrally with or separately from the speaker.

The display device 160, which is a device for visually showing information to a user of the electronic device 101, for example, may include a display, a hologram device, or a projector and a control circuit for controlling the corresponding device. According to an embodiment, the display device 160 may include touch circuitry or a pressure sensor that can measure the intensity of pressure by a touch.

The audio module 170, for example, can bidirectionally convert sound and an electrical signal. According to an embodiment, the audio module 170 can acquire a sound through the input device 150 or can output a sound through the sound output device 155 or an external electronic device (e.g., the electronic device 102 (e.g., a speaker or a headphone) connected to the electronic device 101 through a wire or wirelessly.

The sensor module 176 can generate an electrical signal or a data value corresponding to the operation state (e.g., power or temperature) in the electronic device 101 or an external environmental state. The sensor module 176, for example, may include a gesture sensor, a gyro sensor, a barometer sensor, a magnetic sensor, an acceleration sensor, a grip sensor, a proximity sensor, a color sensor, an IR (Infrared) sensor, a biosensor, a temperature sensor, a humidity sensor, or an illumination sensor.

The interface 177 can support a predetermined protocol that allows for connection to an external electronic device (e.g., the electronic device 102) through a wire or wirelessly. According to an embodiment, the interface 177 may include a High Definition Multimedia Interface (HDMI), a Universal Serial Bus (USB) interface, an SD card interface, or an audio interface.

A connection terminal 178 may include a connector that can physically connect the electronic device 101 with an external electronic device (e.g., the electronic device 102), such as an HDMI connector, a USB connector, an SD card connector, or an audio connector (e.g., a headphone connector).

The haptic module 179 can convert an electrical signal into a mechanical stimulus (e.g. vibration or movement) or an electrical stimulus that a user can recognize through the sensor touch or the sensation of movement. The haptic module 179, for example, may include a motor, a piezoelectric device, or an electric stimulator.

The camera module 180 can take still images and moving images. According to an embodiment, the camera module 180 may include one or more lenses, an image sensor, an image signal processor, or a flash.

The power management module 188, which is a module for managing the power that is supplied to the electronic device 101, for example, may be at least a part of a Power Management Integrated Circuit (PMIC).

The battery 189, which is a device for supplying power to one or more components of the electronic device 101, for example, may include a primary battery that is not rechargeable, a secondary battery that is rechargeable, or a fuel cell.

The communication module 190 can establish a wired or wireless communication channel between the electronic device 101 and an external electronic device (e.g., the electronic device 102, the electronic device 104, or the server 108), and can support communication through the established communication channel. The communication module 190 may include one or more communication processors that support wired communication or wireless communication that is operated independently from the processor 120 (e.g., an application processor). According to an embodiment, the communication module 190 may include a wireless communication module 192 (e.g., a cellular communication module, a near field communication module, or a Global Navigation Satellite System (GNSS) communication module) or a wired communication module 194 (e.g., a Local Area Network (LAN) communication module or a power line communication module). Further, the communication module 190 can communicate with an external electronic device through the first network 198 (e.g., a LAN such as Bluetooth, Wi-Fi direct or Infrared Data Association (IrDA)) or through the second network 199 (e.g., a wide area network such as a cellular network, the internet, or a computer network (e.g., a LAN or a WAN), using the corresponding network. The various communication modules 190 described above may be implemented in one chip or separate chips.

According to an embodiment, the wireless communication module 192 can identify and authenticate the electronic device 101 in a communication network, using user information stored in the subscriber identifier module 196.

The antenna module 197 may include one or more antennas for transmitting or receiving signals or power to or from the outside. According to an embodiment, the communication module 190 (e.g., the wireless communication module 192) can transmit or receive signals to or from an external electronic device through an antenna suitable for the communication method.

Some of the components can be connected to each other and exchange signals (e.g., commands or data) with each other through communication methods among peripheral devices (e.g., a bus, a General Purpose Input/Output (GPIO), a Serial Peripheral Interface (SPI), or a Mobile Industry Processor Interface (MIPI).

According to an embodiment, commands or data can be transmitted or received between the electronic device 101 and the external electronic device 104 through the server 108 connected to the second network 199. The electronic devices 102 and 104 may be the same kind of device as the electronic device 101, or may be different therefrom. According to an embodiment, all or some of the operations of the electronic device 101 may be performed by another one or a plurality of external electronic devices. According to an embodiment, when the electronic device 101 has to perform a function or service automatically or due to a request, the electronic device 101 may request at least partial function related to the function or service from an external electronic device additionally or instead of performing the function or service by itself. The external electronic device receiving the request can perform the requested function or an additional function and transmit the result to the electronic device 101. The electronic device 101 can provide the requested function or service on the basis of the received result or by additionally processing the received result. To this end, for example, cloud computing, distributed computing, or client-server computing may be used.

Figure 2:
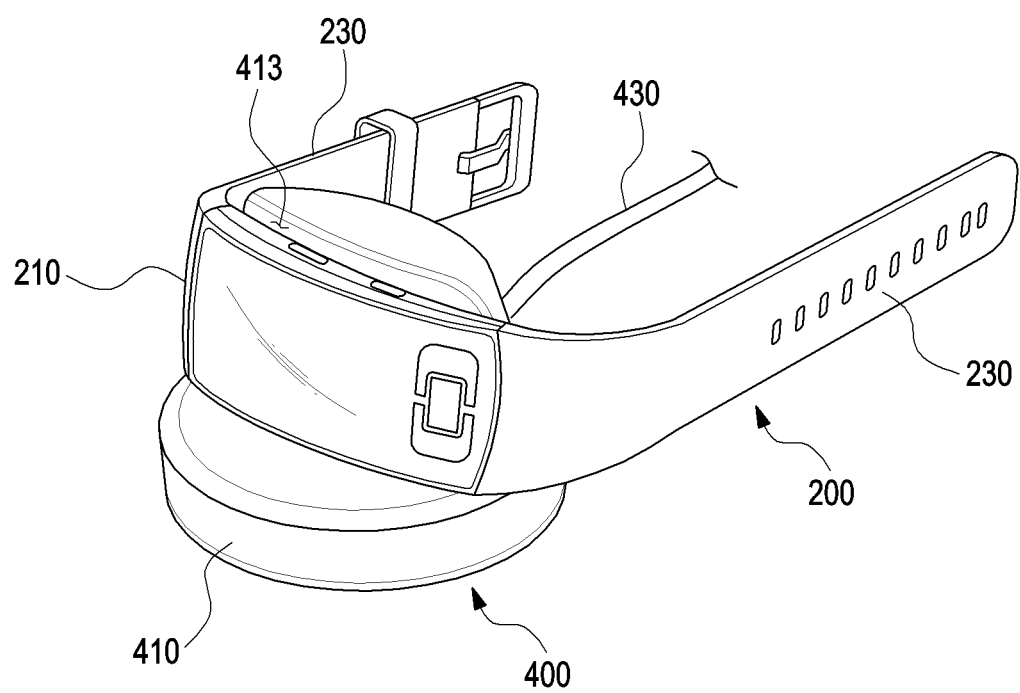
FIG. 2 is a perspective view of a charging module system showing the charging sates of a first electronic device 200 and a second electronic device 400 according to one of various embodiments.

FIG. 2 is a perspective view of a charging module system showing the charging states of a first electronic device 200 and a second electronic device 400 according to one of various embodiments.

Referring to FIG. 2, a charging module system according to one of various embodiments may include the first electronic device 200 and the second electronic device 400. The first electronic device 200 may be a device designed to be worn on a human body and the second electronic device 400 may be a charging module that charges a battery in the first electronic device 200 (e.g., the battery 189 of FIG. 1). The first electronic device 200 and the second electronic device 400 of FIG. 2 may be partially or entirely the same in configuration as the electronic device 101 and the electronic device 102 of FIG. 1, respectively.

According to an embodiment, the first electronic device 200 may be any one of a common analog watch or a common digital watch that is worn on the wrist of a user and wearable electronic devices such as a smart watch and a biometric sign measuring device. The first electronic device 200 may include the body 210 (a function unit) and a holder 230 having a holding member (including a band or a strap). The body 210 may be a watch module of an analog watch or a digital watch, or may be the display device of a wearable electronic device and a module having various multi-functions, or may be a module for sensing biometric signs or various modules for sensing motions of a user. As another example, the display device of a wearable electronic device may function as an input device by being integrated with a touch panel. Alternatively, when the body 210 is a biometric sign sensing module, it may include a sensor for sensing motions of a user or an electrode pad for measuring the heartbeats of a user.

According to various embodiments, the second electronic device 400 may be a charging module that supplies power for charging the battery of the first electronic device 200 (e.g., the battery 189 of FIG. 1) by coming in contact with the first electronic device 200. The second electronic device 400 may include a body 410 having a seat 413 where at least a portion of the rear surface and/or side surfaces of the first electronic device 200 are seated, and a cable 430 that is connected to an external power. According to various embodiments, the cable 430 may be detachably connected to the second electronic device 400. A charging electrode exposed through the seat 413 can be brought in contact with at least one electrode exposed out of the first electronic device 200, so the battery of the first electronic device 200 (e.g., the battery 189 of FIG. 1) can be charged.

Figure 3:
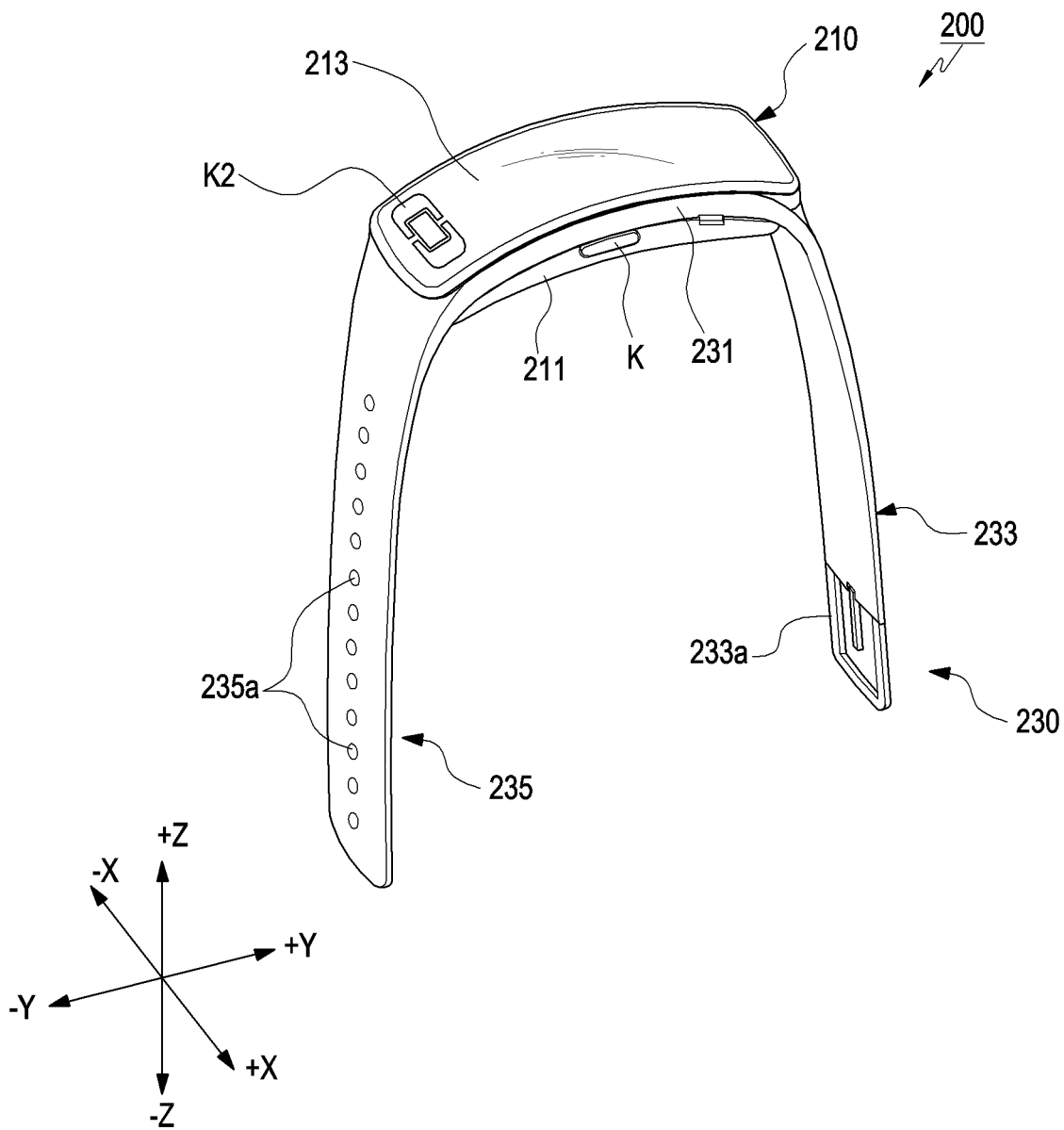
FIG. 3 is a perspective view showing the first electronic device 200 according to one of various embodiments.
Figure 4:
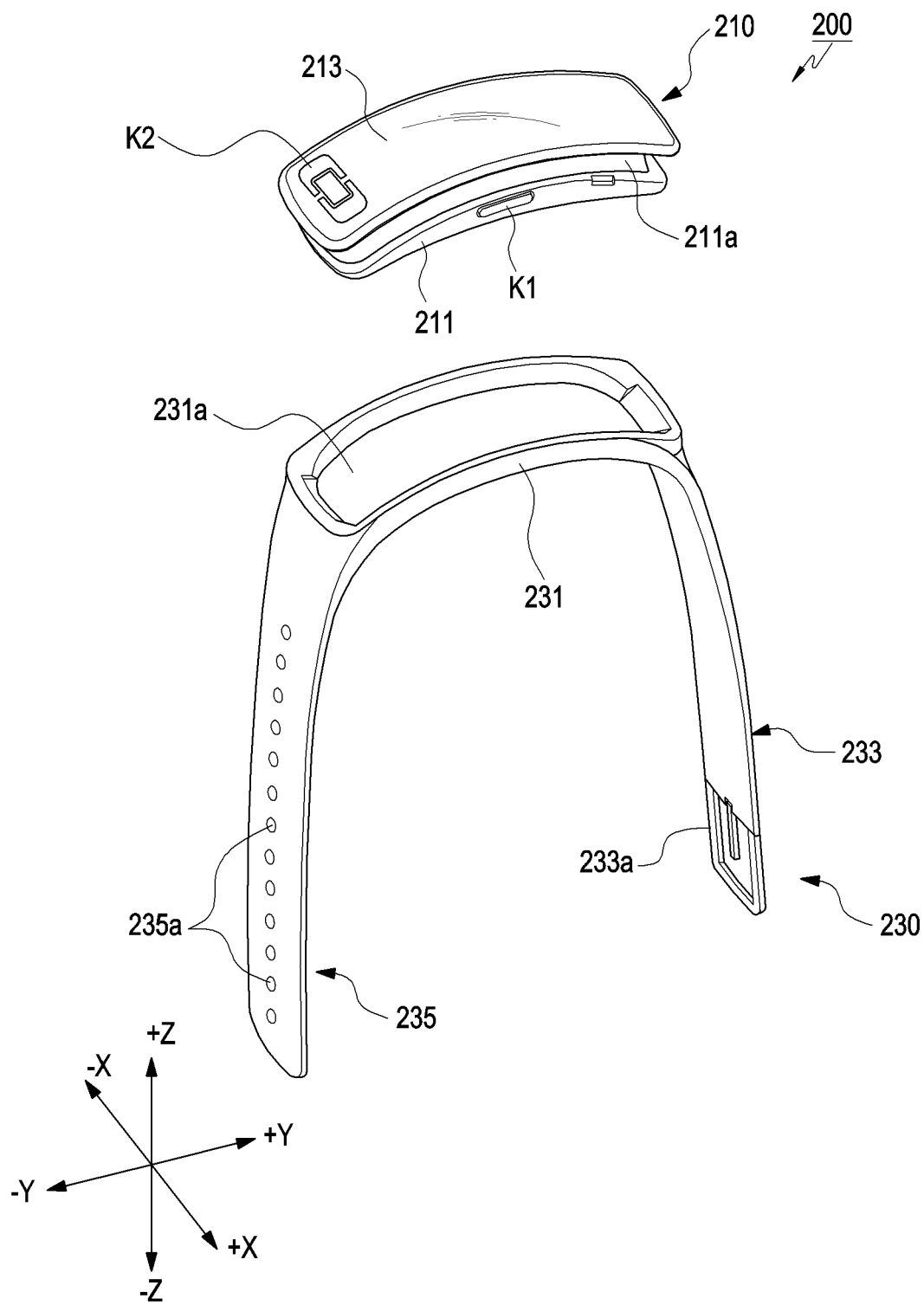
FIG. 4 is a perspective view showing a body 210 of the first electronic device 200 separated from a holder 230 according to one of various embodiments.
Figure 5:
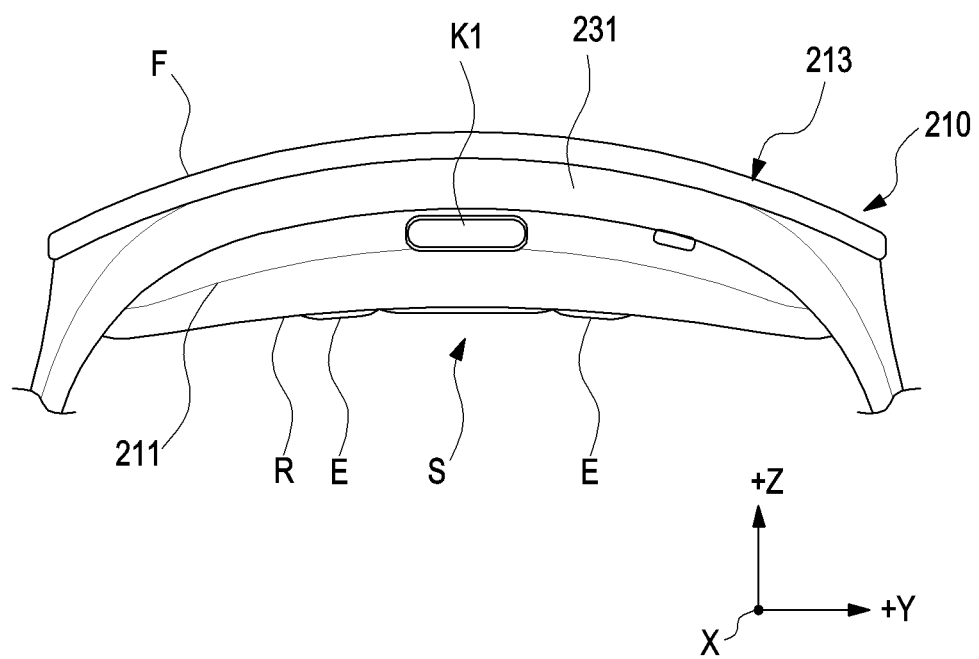
FIG. 5 is a side view showing the body 210 of the first electronic device 200 according to one of various embodiments.

FIG. 3 is a perspective view showing the first electronic device 200 according to one of various embodiments. FIG. 4 is a perspective view showing a body 210 of the first electronic device 200 separated from a holder 230 according to one of various embodiments. FIG. 5 is a side view showing the body 210 of the first electronic device 200 according to one of various embodiments.

In the rectangular coordinate system shown in FIGS. 3 to 5, 'X' may mean the width direction of the body 210 of the first electronic device 200, 'Y' may mean the length direction of the body 210, and 'Z' may mean the thickness direction of the body 210. Further, in an embodiment, 'Z' may mean a first direction (+Z) and a second direction (−Z), 'Y' may mean a third direction (+Y) and a fourth direction (−Y), and 'X' may mean a fifth direction (+X) and a sixth direction (−X).

This embodiment shows a wearable device, for example, an electronic device that can be worn on a wrist such as a watch or a bracelet as the first electronic device 200. However, various embodiments are not limited thereto and electronic embodiments according to various embodiments may be various communication devices or assistant medical devices. The first electronic device 200 according to various embodiments can be variously applied to curved parts of the body of a user. For example, the curved parts of the body of a user may be the wrist or the ankle. Further, electronic devices according to various embodiments can be conveniently worn on various parts of the body of a user, depending on the configuration of wearing parts.

Referring to FIGS. 3 to 5, the first electronic device 200 may include the body 210 (a function unit) and the holder 230 having a holding member (including a band or a strap).

According to various embodiments, the body 210 can be separably combined with the holder 230. A display device 213 for displaying various items of information (e.g., the display device 160 of FIG. 1), a key for inputting various items of information (e.g., a side key K1, a front key K2), a biometric sensor S (e.g., a biometric sign sensor), a plurality of electrodes E, or a touch input unit may be disposed in the body 210. The body 210 may have a front surface F facing the first direction (+Z) and a rear surface R facing the second direction (−Z) in which the rear surface R is brought in contact with the body of a user when worn on the body. The display device 213 may be disposed on the front surface F of the body 210, and the biometric sensor S and the electrodes E may be disposed on the rear surface R of the body 210.

According to various embodiments, the body 210 is formed in a bar shape and may at least partially have curvature corresponding to the body of a user. For example, the body 210 may be formed in a rectangular shape extending substantially in the length direction (+Y, −Y axis direction) and may have curvature. A fitting groove for coupling to the holder 230 may be formed at each of side surfaces of the body 210. A plurality of fitting grooves may be formed at the side surfaces of the body 210 or a fitting groove may be formed in a closed curve shape around the body 210. However, the shape of the body 210 is not limited to a rectangular shape and may be changed in various shapes in consideration of the user's preference and/or the arrangement relationship of internal parts.

According to various embodiments, the holder 230 is made of an elastic material so that the body 210 can be stably worn on the body of a user, and if necessary, the body 210 may be brought in close contact with the skin of the user's body. Further, the body 210 is separably combined with the holder 230, so the holder 230 can be replaced in accordance with the individuality or taste of users. In another embodiment, the portion (e.g., the seat 231), which is combined with the body 210, of the holder 230 may be elastically deformed and holding portions that are brought in close contact with the body of a user (e.g., the inner sides of the first and second holding members 233 and 235) may not be made of an elastic material. The holder 230 may have an opening 231a extending in a predetermine direction to separably retain the body 210. The seat 231 surrounds the opening 231a and at least the seat 231 of the holder 230 may be made of an elastic material. When the body 210 is combined with the holder 230, at least a portion of the seat 231 can be fitted in the fitting groove extending around the side surfaces of the body 210.

According to various embodiments, the opening 231a is an open space in which the body 210 is fitted, and is surrounded by the seat 231. For example, the opening 231a may be formed in a rectangular shape substantially having a thickness. When seen from above, the opening 231a may have a rectangular shape that is longer in the length direction (+Y, −Y direction) than the width direction (+X, −X direction). Furthermore, the holder 230 may have a linear portion surrounding the opening 231a, for example, the seat 231. The first and second holding members 233 and 235 may extending from the edge of the opening 231a, for example, from at least a portion of the seat 231 away from each other in the length direction Y of the body 210. Alternatively, considering that the first electronic device 200 is supposed to be worn on the body of a user, the first and second holding members 233 and 235 may be curved in the thickness direction Z of the width direction of the body 210 with respect to the seat 231. However, the shape of the opening 231a is not limited to a rectangular shape and may be formed in various shapes corresponding to the various shapes of the body.

According to various embodiments, the holder 230 may have a fastener for fastening the first and second holding members 233 and 235. For example, a first fastening member 233a may be disposed at the first holding member 233 and a plurality of fastening holes 235a may be formed at the second holding member 235. The fastening holes 235a are arranged in the extension direction of the second holding member 235 and can be fitted to the first fastening member 233a. The first fastening member 233a is fitted in one of the fastening hole 235a, thereby fastening the first and second holding members 233 and 235 to each other, so the holder 230 can be maintained in closed curve shape. However, the fastening structure is just one of embodiments and can be replaced with various other structures (e.g., a snapping structure), depending on the material and structure of the first and second holding members 233 and 235.

According to various embodiments, the first electronic device 200 may include a body housing 211 forming the outer side of the body 210 and the body housing 211 may have a shape with curvature. Since the seat 231 is made of an elastic material and elastically deformed, it can be fitted on the body housing 211 by deforming to corresponding to the shape of the body housing 210, for example, the shape of the fitting groove 211a. The holder 230 has a changeable structure, so users can replace and use various holders by applying various designs and colors in accordance with their tastes. That is, the holder 230 can be used as an accessory showing the individuality of the user.

According to various embodiments, the body 210 has a shape (e.g., a substantially rectangular shape) corresponding to the seat 231 (or the opening 231a) and the first electronic device 200 can activate various different functions, depending on the direction in which the body 210 is coupled to the holder 230. In general, since the size and curvature of users' wrists are different, they may feel different fit when they wear electronic devices having the same shape. For example, since men generally have a thicker wrist than women, it may be difficult to provide the same comfortable fit to all users when they wear the same wearable devices. However, the first electronic device 200 according to various embodiments has the structure in which the body 210 and the holder 230 are separably combined, so users can comfortably wear the electronic device by selecting an appropriate holder 230 suitable for his/her body.

Figure 6:
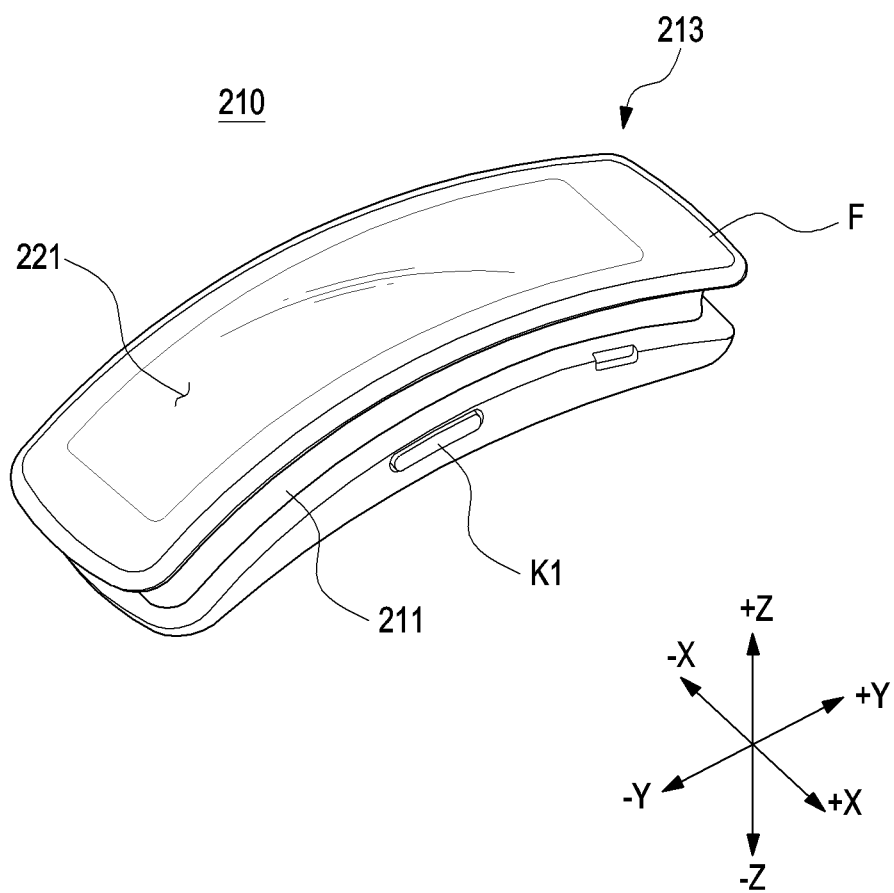
FIG. 6 is a perspective view showing the front surface of the body 210 of the first electronic device according to one of various embodiments.
Figure 7:
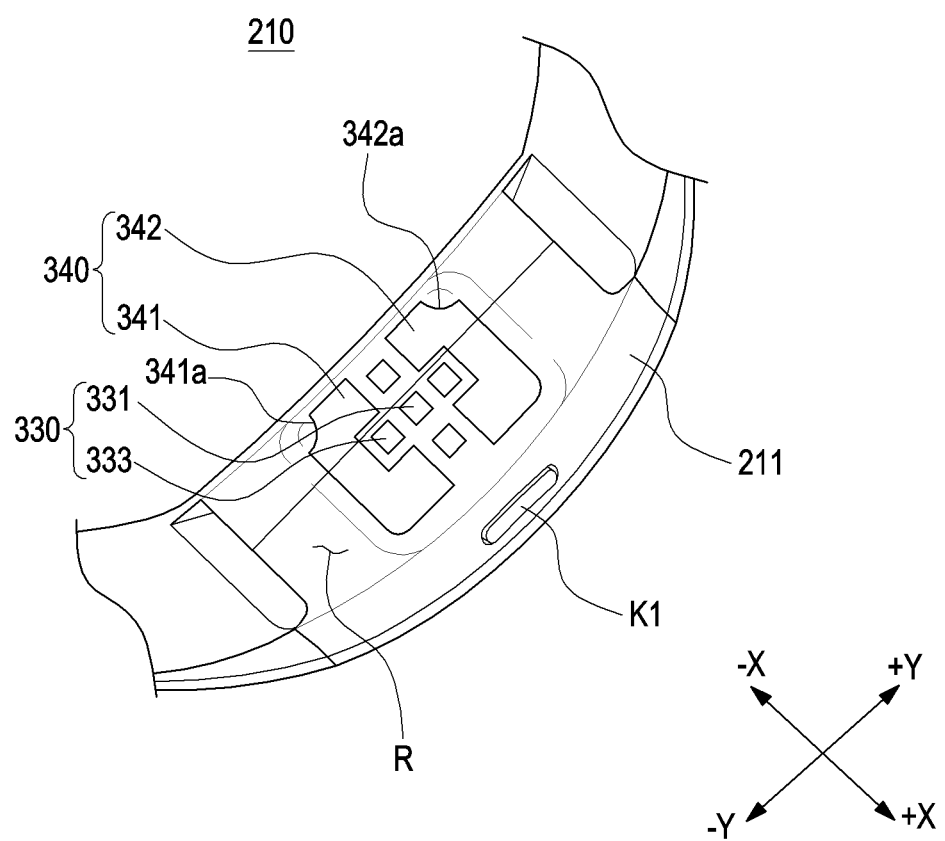
FIG. 7 is a perspective view showing the rear surface of the body 210 of the first electronic device according to one of various embodiments.
Figure 8:
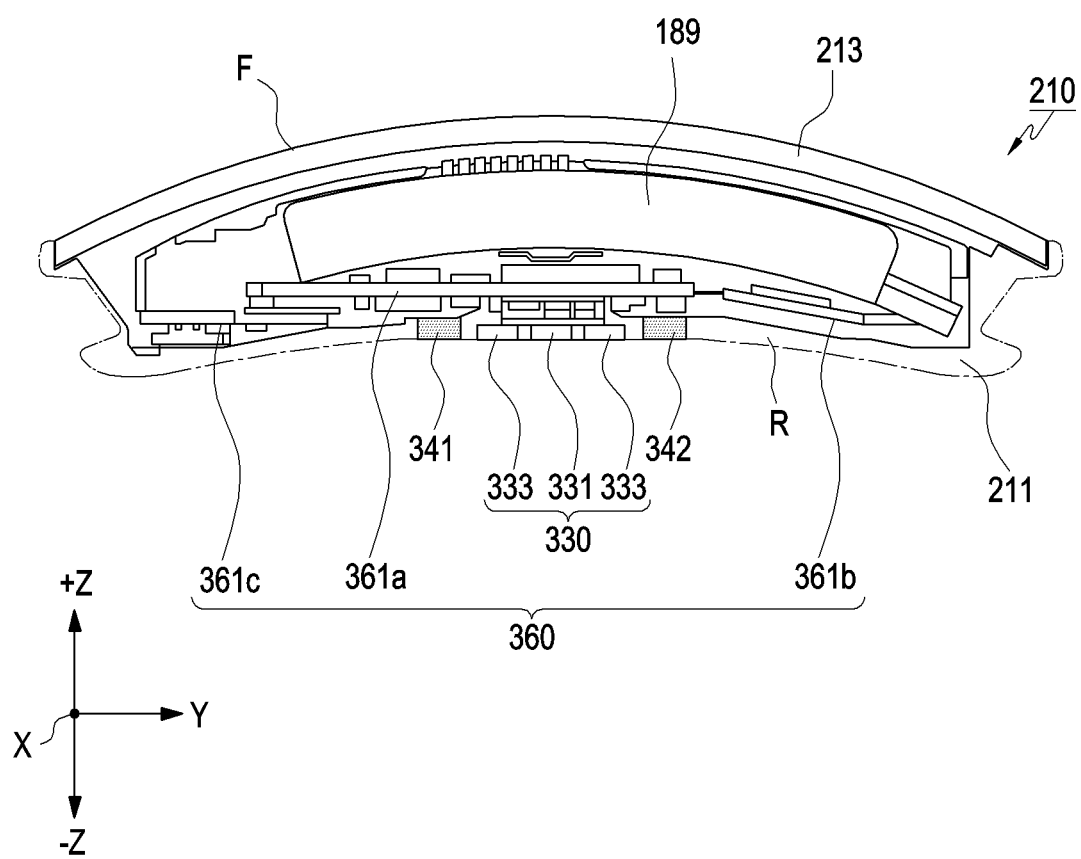
FIG. 8 is a vertical cross-sectional view showing the internal configuration of the body 210 of the first electronic device according to one of various embodiments.

FIG. 6 is a perspective view showing a body 210 of a first electronic device 200 according to one of various embodiments. FIG. 7 is a perspective view showing the body 210 of the first electronic device according to one of various embodiments in another direction. FIG. 8 is a vertical cross-sectional view showing internal configuration of the body 210 of the first electronic device 200 according to one of various embodiments.

In the rectangular coordinate system shown in FIGS. 6 to 8, "X" may mean the width direction of the body of the first electronic device 200, "Y" may mean the length direction of the body 210, and "Z" may mean the thickness direction of the body 210. Further, in an embodiment, 'Z' may mean a first direction (+Z) and a second direction (−Z), 'Y' may mean a third direction (+Y) and a fourth direction (−Y), and 'X' may mean a fifth direction (+X) and a sixth direction (−X).

Referring to FIGS. 6 to 8, the body 210 of the first electronic device has a long rectangular bar shape elongated in the longitudinal direction with curvature. The body 210 may include a body housing 211, a display device 213 mounted on the body housing 211, a biometric sensor 330 and a plurality of electrodes 340 that are disposed in the body housing 211, a battery 189, and a circuit board 360. Some or all of the body housing 211, the display device 213, and the biometric sensor 330 of the first electronic device 200 of FIGS. 6 to 9 may be the same as the body housing 211, the display device 213, and the biometric sensor S of the first electronic device 200 of FIGS. 3 to 5.

According to various embodiments, the body housing 211 has a front surface F, a rear surface R, and side surfaces connecting the front surface F and the rear surface R, and the front surface F and the rear surface R may be curved. The front surface F of the body housing 211 is a surface where the display device 213 is disposed and the rear surface R of the body housing 211 is a contact surface that comes in contact with the body of a user. The front surface F may have first curvature and the rear surface R may have second curvature. The first and second curvatures may be determined in consideration of the design of the product, the circumference of the user's wrist, and the fit. In the embodiment, the first curvature is smaller than the second curvature.

According to various embodiments, the body housing 211 has appropriate curvature (e.g., the second curvature) in consideration of the shape of the body of a user, for example, the thickness and curvature of a wrist, whereby it is possible to improve fit for a user and improve compatibility for various circumferences of the wrists of various customers. The curved display device 213 is disposed on the front surface F of the body housing 211, the biometric sensor 330, for example, a vita signal sensor is disposed on the rear surface R, and the rear surface R can be brought in contact with the body (e.g., wrist) of a user.

According to various embodiments, the display device 213 on the body 210 may be a curved display device having curvature to implement a curved design having curvature and a curved window 321 having curvature the same as the curvature of the curved display may be further included.

According to an embodiment, the display device 213 may be a flexible display being able to form a curved surface, or it may be a flat display, depending on the external shape of the electronic device. The display device 213 may further include a sensing device that senses capacitance, pressure, or temperature by a touch by a user, for example, a touch panel. The touch panel may be integrated with the curved display. The sensing device disposed in the display device 213, a Physical User Interface (PUI) optimized for using various UIs can be provided. The curved window 221 may include a rigid or flexible layer. For example, the curved window 221 may be made of glass or ceramic and may have a layer made of a sheet such as PET and PC to protect the surface.

According to various embodiments, the biometric sensor 330 in the body 210 may be positioned to be exposed toward the rear surface R of the first electronic device 200. For example, the biometric sensor 330 may be positioned very close to the rear side R of the body housing 211 to be able to sense a biometric reaction of a user at a close position.

According to various embodiments, the biometric sensor 330 may be a biometric sign sensor that detects at least one of a Photo Plethysmo Graph (PPG), a sleep interval, skin temperature, and heartbeats of a user.

According to various embodiments, the biometric sensor 300 may be disposed on a circuit board 360 disposed in the body 210 and may be electrically connected with the circuit board 360. For example, the biometric sensor 330 may be disposed on the circuit board 360 to face the second direction (−Z). Accordingly, the biometric sensor 330 can emit light toward the body of a user and receive light reflected by the body of the user. Alternatively, it may be possible to seal other electronic parts and/or the sensor on the circuit board 360 by providing a sealing structure (not shown) around the biometric sensor 330.

According to various embodiments, the biometric sensor 330 may include at least one light source 331 and photodiode 333, and the light sources 331 and photodiodes 333 may be alternately arranged. FIG. 7 shows the rear surface R of the first electronic device 200, in which a light source 331 may be disposed at the center and one or more photodiodes 333 may be disposed around the light source 331.

According to an embodiment, the light source 331 and the photodiodes 333 may be disposed in the same plane. For example, a light source 331 electrically connected with the circuit board 360 may be disposed on a surface facing the second direction (−Z) of the circuit board 360, and a plurality of photodiodes 333 may be disposed at predetermined distances with the light source 331 therebetween. The photodiodes 333 may be disposed on the first surface 351 of the circuit board 360 and electrically connected with the first circuit board 360.

According to various embodiments, the light source 331 can emit light toward the rear surface R of the body housing 211. For example, the light source 331 may be an LED module and can emit light with various colors. The emitted light may have a wavelength range of about 380 nm to 800 nm. Alternatively, the light emitted from the light source 331 may be green light, which may have a wavelength range of about 492 nm to 575 nm. The light source 331 can cap the surrounding portion of the circuit board to protect the internal circuit board to which light is emitted, and the capping material, for example, may be epoxy.

According to various embodiments, the photodiodes 333 can receive and convert reflective light into current when the light emitted from the light source 331 is reflected by the body of a user. For example, in order to measure the heartbeats of a user, when some of the light emitted from the light source 331 is reflected by the current of blood in the blood vessels of the user back to the photodiode 333, the light signal can be converted into a current signal. Alternatively, it is efficient for the photodiodes 333 to have a large area in order to sufficiently receive the reflective light, so a plurality of photodiodes may be disposed at a lower portion around the light source. For example, two photodiode 333 may be disposed at both sides of the light source 331 around the light source 331. Alternatively, four photodiodes 333 may be disposed in the third, fourth, fifth, and sixth direction (+Y, −Y, +X, −X) around the light source 331. However, the arrangement of the photodiodes 333 is not limited thereto and various numbers of photodiodes may be arranged in various ways to be able to efficiently receive reflective light and biometric information of a user.

According to various embodiments, the biometric sensor 330 may be disposed between the circuit board 360 and the rear surface R to sense the biometric information of a user. The biometric sensor, for example, may be a sensor that collects or measures one or more biometric signs from a user. The biometric sensor can collect to measure one or more of the blood pressure, a blood stream, a heart rate (HRM, HRV), body temperature, a breathe rate, oxygen saturation, heart and lung sound, blood sugar, waist measurement, height, weight, body fat, consumption of calorie, a brain wave, voice, skin resistance, electromyogram, electrocardiogram, a walk, an ultrasonic wave image, a sleep state, facial expression (face), pupil dilation, and a blink of a user.

According to an embodiment, the electronic device can create biometric information (or referred to as biometric characteristic information) by analyzing biometric signs. For example, a signal that is obtained by a photoplethysmography (PPG) sensor using an optical method to measure a pulse wave signal or an electrocardiography (ECG) sensor using an electrode may be the biometric sensor. The electronic device can obtain primary biometric information such as an average heart rate or heartbeat distribution by analyzing biometric signs and can obtain secondary biometric information such as a higher order stress state or the degree of aging of blood vessels by processing the primary biometric information.

According to an embodiment, the biometric sensor may simply output the collected biometric sign of a user or may output biometric information by analyzing biometric signs through a processor in the biometric sensor (e.g., the processor 120 of FIG. 1). Accordingly, the biometric signs collected by a biometric sensor module can be transmitted to the processor in the biometric sensor module, a processor in an electronic device including the biometric sensor module, or a processor of an external device (e.g., the server 108 or the electronic device 104 of FIG. 1) to be used to produce biometric information.

According to various embodiments, the electrodes 340 may be disposed close to the biometric sensor 330 to be exposed toward the rear surface R of the body housing 211. For example, the electrodes 340 may be disposed opposite to or face each other around the biometric sensor 330. When a user wears the first electronic device (e.g., the first electronic device 200 of FIG. 2), the electrodes 340 can be hidden by the body 210 or the body of the user.

According to various embodiments, the electrodes 340 can be used to charge the battery 189 in the first electronic device 200 or measure biometric signs. For example, the electrodes 340 may be formed in a wired charging type by contact with the charging electrodes of the second electronic device (e.g., the second electronic device 400 of FIG. 2) to charge the battery 189. Alternatively, the electrodes 340 may be used as pads for measuring an electroradiogram by being electrically connected with the biometric sensor 330 to measure biometric signs.

According to various embodiments, the electrodes 340 may include a first electrode 341 and a second electrode 342 disposed at both sides of the biometric sensor 330. For example, the first electrode 341 and the second electrode 342 may be disposed at least partially around the biometric sensor 330. The first electrode 341 and the second electrode 342 may be disposed in a flat area of the rear surface R of the body 210 to come in close contact with the body of a user.

According to an embodiment, the first electrode 341 may be disposed close to an end, which faces the third direction (+Y), of the biometric sensor 330 and may be formed in a plate shape having different lengths. For example, the first electrode 341 may be disposed in an as wide area as possible on the rear surface of the body housing 211 for strong coupling to a biometric sign measuring and/or charging module (e.g., the second electronic device 400 of FIG. 2). The first electrode 341 may be disposed with different lengths in the third direction (+Y) and/or the fourth direction (−Y) to be disposed in most area except for the area of the biometric sensor 330 on the rear surface of the body housing 211. The central area may be partially recessed so that the length of the central area of the first electrode 341 in the biometric sensor 330 is disposed is smaller than that of the surrounding area. For example, the first electrode 341 may be formed in a [-shape with the central area removed.

According to an embodiment, the second electrode 342 may be disposed close to an end, which faces the fourth direction (−Y), of the biometric sensor 330 and may be formed in a plate shape having different lengths. The second electrode 342 may be spaced a predetermined distance from the first electrode 341. For example, the second electrode 342 may be disposed in an as wide area as possible on the rear surface of the body housing 211 for strong coupling to a biometric sign measuring and/or charging module (e.g., the second electronic device 400 of FIG. 2). The second electrode 342 may be disposed with different lengths in the third direction (+Y) and/or the fourth direction (−Y) to be disposed most area except for the area of the biometric sensor 330 on the rear surface of the body housing 211. The central area may be partially recessed so that the length of the central area in the biometric sensor 330 is disposed is smaller than that of the surrounding area. For example, the second electrode 342 may be formed in a ]-shape with the central area removed.

According to an embodiment, the first electrode 341 and the second electrode 342 may be disposed to have different polarities. For example, when the first electrode 341 forms a positive (+) pole, the second electrode 342 may form a negative (−) pole. Alternatively, when the first electrode 341 forms a negative (−) pole, the second electrode 342 may form a positive (+) pole.

According to an embodiment, the first electrode 341 and the second electrode 342 may include a material having magnetism. The first electrode 341 and the second electrode 342 may include a material having high conductivity, strong magnetic force, and high anticorrosion for self-alignment between the second electronic device (e.g., the second electronic device 400 of FIG. 2) and a device. Further, they may be made of a material that less influences the skin because they are supposed to come in direct contact with the skin of a user. For example the first electrode 341 and the second electrode 342 may be made of a material including ferritic stainless steel.

According to various embodiments, the electrodes 340 may have a notch structure having at least partial area protruding or recessed along the rear surface of the body housing 211. For example, the first electrode 341 may have a first notch 341a recessed inward at at least a portion of the side facing the third direction (+Y). The first notch 341a may be formed at a corner of the first electrode 341. Alternatively, the second electrode 342 may have a second notch 342a recessed inward at at least a portion of the side facing the fourth direction (−Y). The second notch 342a may be formed at a corner of the second electrode 342. The notch structure can be used for self-alignment between the second electronic device and a device.

According to an embodiment, the first notch 341a of the first electrode 341 and the second notch 342a of the second electrode 342 may be both formed in the longitudinal direction of the housing or may be formed in opposite directions. The arrangement structure of the first notch 341a of the first electrode 341 and the second notch 342a of the second electrode 342 may be defined in various ways to correspond to the arrangement of the charging electrode of the second electronic device (e.g., the second electronic device 400 of FIG. 2), which will be described below (with reference to FIGS. 12A to 13B).

According to various embodiments, the battery 189 is disposed in an internal space of the body housing 211 and may be electrically connected with the electrodes 340 through the circuit board 360.

According to various embodiments, the battery 189 is curved to be disposed in the center of the curved display device 213, so electronic components can be efficiently disposed in the body 210. For example, mounting spaces can be secured at both ends of the battery 189 in the body housing 211. This mounting structure reduces the thickness at both ends relative to the center of the body housing 211, so an aesthetic design can be achieved. Further, the rear surface R of the body housing 211 is formed to be able to sufficiently come in contact with the body of a user, so hardware components can be optimally mounted.

According to various embodiments, the battery 189 has a flexible printed circuit board (not shown), so it can be connected to the printed circuit board 360 and can supply power to the printed circuit board 360. The display device 213, the curved battery 189, and at least one circuit board 360 having various electronic components may be vertically stacked. For example, the battery 189 may be disposed between the display device 213 and the circuit board 360. Accordingly, it is possible to secure a safety means that can suppress damage to a user such as a low-temperature burn due to damage and heat of the battery 189.

According to various embodiments, the circuit board 360 can be disposed in the body housing 211. The circuit board 360 has a segmented structure composed of a plurality of segmented substrates 361a, 361b, and 361c, so electronic components can be efficiently mounted. The circuit board 360 having a segmented structure appropriately provides hard substrates and soft substrate in necessary sections, so the substrates can be disposed or arranged to correspond to a curved design. Further, the substrates are disposed in the segments in consideration of the operation environment of the electronic components, so the performance of the first electronic device (e.g., the first electronic device 200 of FIG. 2) can be optimized. For example, it is possible to separately dispose components that are vulnerable to noise and components that cause noise on different substrates and separately dispose components that are weak to shock and components that cause shock on different substrates. According to this arrangement of the electronic components, it is possible to naturally separate a noise-generating section and a noise-sensitive section and it is also possible block vibration shock that is transmitted through the hard substrate to the soft substrate section. Accordingly, it is possible to optimize the electrical performance and durability of the electronic device. Other than fundamental communication and input/output-related components, non-contact type sensors such as a gyro sensor, an acceleration sensor, and other optical sensors can be further mounted on the circuit board 360 having the segmented structure.

According to an embodiment, the substrates 361, 361b, and 361c of the circuit board 360 can be separated. In the electronic components mounted on the first, second, and third substrates 361, 361b, and 361c, components that are vulnerable to noise (e.g., a Power Amplifier Module (PAM)) and components that cause noise (e.g., an Application Processor (AP) and a Communication Processor (CP)) can be separately disposed on the first and second substrates 361a and 361b. Further, components that are weak to shock (e.g., Ball Grid Arrays (BGA) such as an AP and CP) and components that cause shock (e.g., a vibrator including a vibration module) can be separately disposed on the second and third substrate 361b and 361c. According to this arrangement of the electronic components, it is possible to naturally separate a noise-generating section and a noise-sensitive section and it is also possible block vibration shock that is transmitted through the hard substrate to the soft substrate section. Accordingly, it is possible to optimize the electrical performance and durability of the electronic device.

According to an embodiment, at least one of the first, second, and third substrates 361, 361b, and 361c disposed on the rear surface R of the body housing 211 may be positioned horizontally or at an angle. The first substrate 361a, which is disposed at the middle, has the biometric sensor 330, for example, a biometric sign sensor thereon, so it can be horizontally positioned together with the biometric sensor 330. The biometric sensor 330 is exposed on the rear surface R of the body housing 211 and may be horizontally positioned at the portion that can come in closest contact with the skin of the user's body, that is, substantially at the central area of the rear surface R of the body housing 211.

Figure 9:
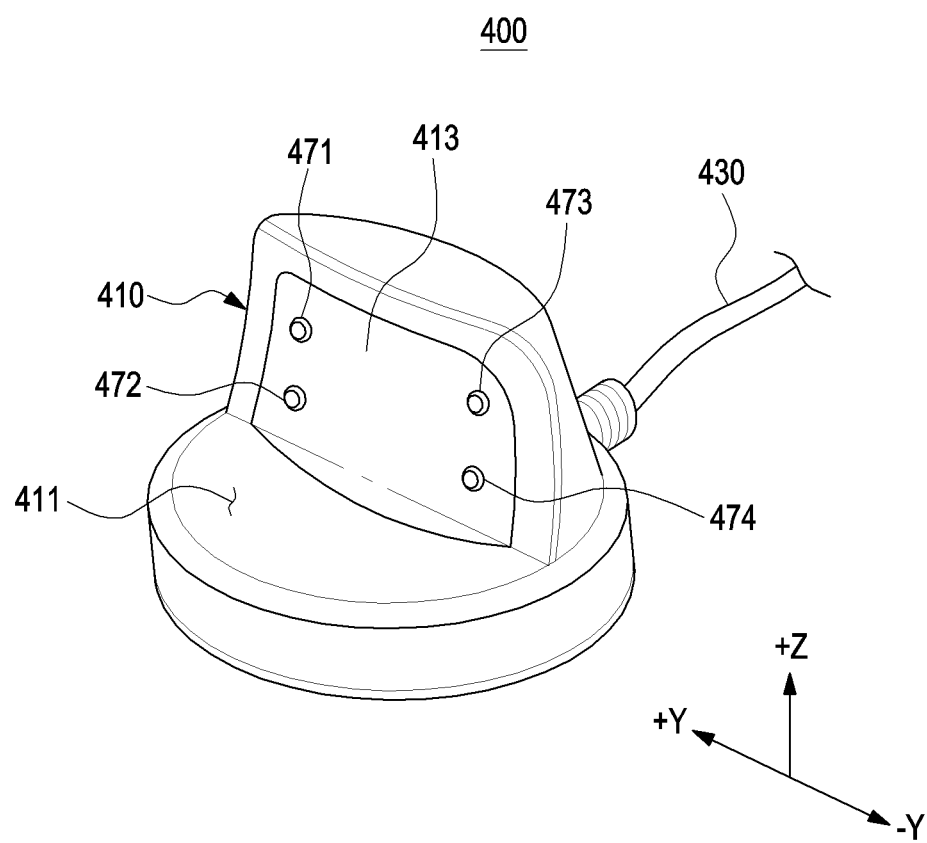
FIG. 9 is a perspective view showing a charging area of the second electronic device 400 according to an embodiment.
Figure 10:
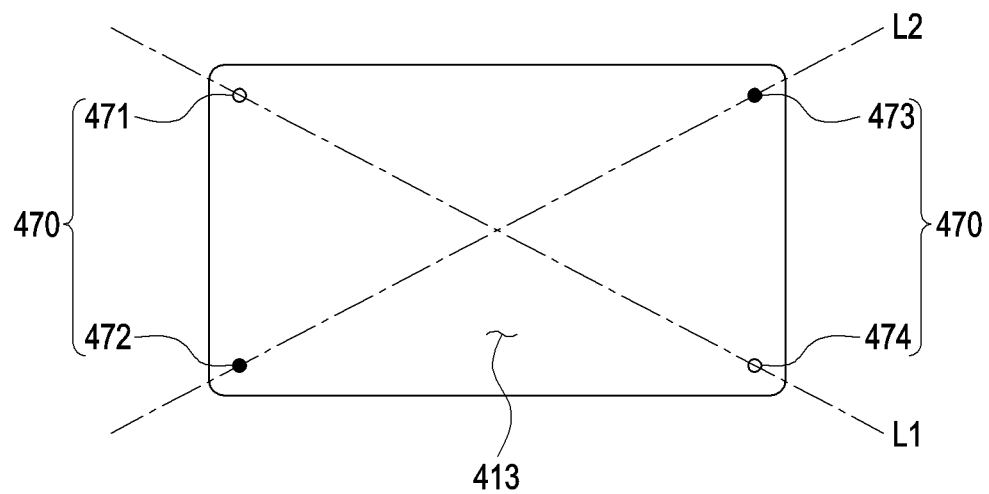
FIG. 10 is a view showing an arrangement relationship of charging electrodes in the charging area of the second electronic device 400 according to an embodiment.
Figure 11:
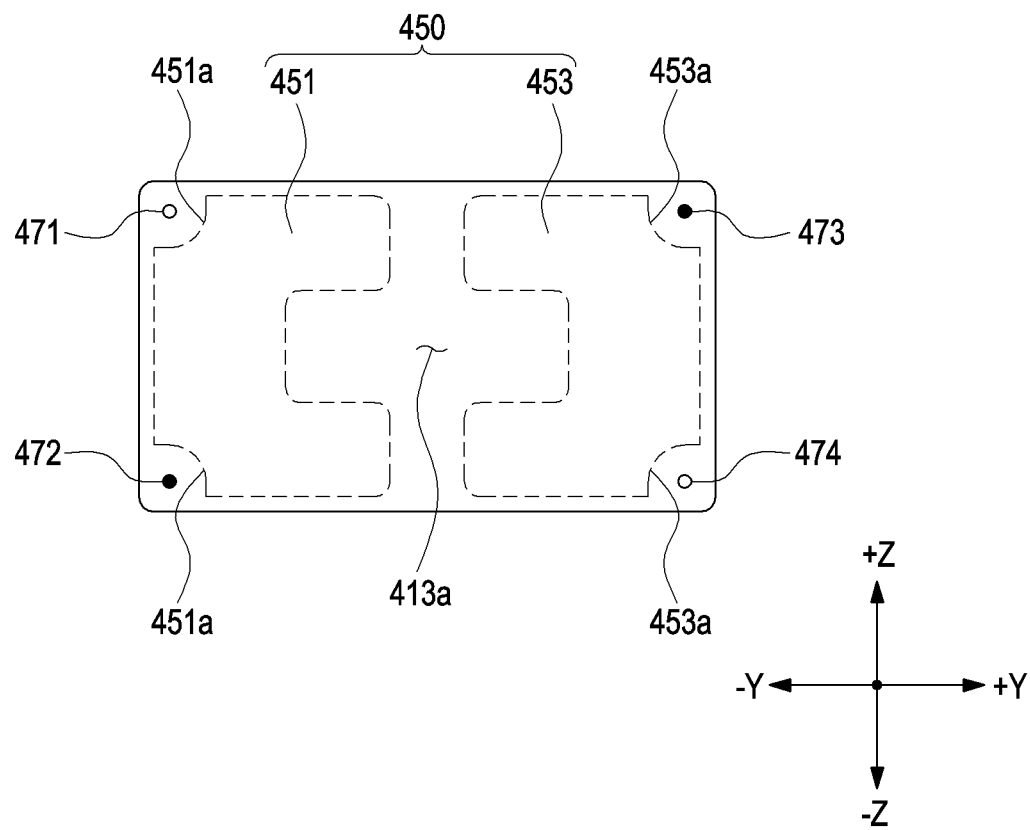
FIG. 11 is a projective view showing an arrangement relationship of internal magnets in the charging area of the second electronic device 400 according to an embodiment.

FIG. 9 is a perspective view showing a charging area of the second electronic device 400 according to an embodiment. FIG. 10 is a view showing an arrangement relationship of charging electrodes in the charging area of the second electronic device 400 according to an embodiment. FIG. 11 is a projective view showing an arrangement relationship of internal magnets in the charging area of the second electronic device 400 according to an embodiment.

Referring to FIGS. 9 to 11, the second electronic device 400 may include a housing 410, a magnet 45 disposed in the housing 410, and a plurality of charging electrodes 470 disposed close to the magnet 450. The second electronic device 400 may be a charging module that supplies power for charging the battery 189 of the first electronic device 200 by coming in contact with the first electronic device (e.g., the first electronic device 200 of FIG. 2). The second electronic device 400 of FIGS. 9 to 11 may be partially or entirely the same as the second electronic device 400 of FIG. 2.

In the two-axial rectangular coordinate system shown in FIGS. 9 to 11, "Z" may mean the width direction of a seat 413 of the housing 410 of the second electronic device 400 and "Y" may mean the length direction of the seat 413 of the housing of the second electronic device 400. Further, in an embodiment, 'Z' may mean a first direction (+Z) and a second direction (−Z) and 'Y' may mean a third direction (+Y) and a fourth direction (−Y).

According to an embodiment, the housing 410 may have a supporting surface 411 that supports at least a portion of a first electronic device (e.g., the first electronic device 200 of FIG. 2) and a seat 413 that has contact points for charging the battery of the first electronic device.

According to various embodiments, the housing 410 forms the body of the second electronic device 400, and for example, it may be made of a metallic material and/or a nonmetallic material (e.g., polymer). The supporting surface 411 can support a side of the first electronic device by providing a surface facing the first direction (+Z) and the seat 413 extends from the supporting surface 411, provides a surface facing the direction perpendicular to the first direction (+Z), and can face the rear surface (e.g., the rear surface R of FIG. 2) of the first electronic device (e.g., the first electronic device 200 of FIG. 2). A cable 430 that is connected to an external power supply may be exposed from the outer side of the housing 410. According to various embodiments, the cable 430 can be separably connected to the second electronic device 400. According to various embodiments, the magnet 450 is disposed inside the housing 410 and can attach the first electronic device (e.g., the first electronic device 200 of FIG. 2) to the seat 413 of the housing 410 by being magnetically combined with the first electronic device. For example, the magnet 450 is formed in plates shape and may be disposed inside the seat 413 to face the seat 413.

According to various embodiments, a plurality of magnets 450 may be spaced at a predetermined distance from each other with the central area of the seat 413 therebetween not to face a biometric sensor of the first electronic device (e.g., the first electronic device 200 of FIG. 2). For example, the magnets 450 may be formed and disposed in a shape corresponding to a plurality of electrodes (e.g., the electrodes E of FIG. 5) of the first electronic device (e.g., the first electronic device 200).

According to various embodiments, the magnets 450 may include a first magnet 451 and a second magnet 453 spaced from the first magnet 451. According to an embodiment, the first magnet 451 may be formed along at least a portion around the central area 413a of the seat 413. The first magnet 451 may be formed in a plate shape having different lengths in the longitudinal direction of the seat 413. For example, the first magnet 451 may be disposed in the widest area for strong coupling to the first electronic device (e.g., the first electronic device 200 of FIG. 2). The first magnet 451 may be formed such that the length facing the central area 413a of the seat 413 is smaller than the length of the other area. For example, the first magnet 451 may be formed in a [-shape with the central area 413a removed.

Alternatively, the second magnet 453 may be formed along at least a portion around the central area 413a of the seat 413. The second magnet 453 may be formed in a plate shape having different lengths in the longitudinal direction of the seat 413. For example, the second magnet 453 may be disposed in the widest area for strong coupling to the first electronic device (e.g., the first electronic device 200 of FIG. 2). The second magnet 453 may be formed such that the length facing the central area 413a of the seat 413 is smaller than the length of the other area. For example, the first magnet 451 may be formed in a ]-shape with the central area 413a removed.

According to various embodiments, the magnets 451 and 453 may have a notch structure having at least partial area protruding or recessed in the length direction. For example, the first magnet 451 may have notches 451a recessed at portions of the outer corners facing the fourth direction (−Y). The notches 451a may be formed at both ends and charging electrodes 471 and 472 having different polarities may be disposed close to the notches 451a. As another example, the second magnet 453 may have notches 453a recessed at portions of the outer corners facing the third direction (+Y). The notches 453a may be formed at both ends and charging electrodes 473 and 474 having different polarities may be disposed close to the notches 453a. The notches 451a and 453a and the charging electrodes 471, 472, 473, and 474 disposed close to the notches can be used for self-alignment between the first electronic device (e.g., the first electronic device 200 of FIG. 2) and the second electronic device 400.

According to an embodiment, the first notch 451a of the first magnet 451 and the second notch 453a of the second magnet 453 may be both formed in the longitudinal direction of the seat 413 or may be formed in opposite directions. The arrangement of the first notch 451a of the first magnet 451 and the second notch 453a of the second magnet 453 may be changed in various ways in accordance with the arrangement of the electrodes of the first electronic device (e.g., the first electronic device 200 of FIG. 2).

According to various embodiments, the charging electrodes 470 may be disposed in the housing 410 and may come in contact with the electrodes of the first electronic device (e.g., the first electronic device 200 of FIG. 2).

According to various embodiments, the charging electrodes 470 include two pairs of a positive (+) pole and a negative (−) pole, that is, a total of four electrodes may be provided. The pairs of a positive (+) pole and a negative (−) pole may be respectively disposed around the first notches 451a of the first magnet 451 and the second notches 453a of the second magnet 453. For example, a pair of charging electrodes 471 and 472 may be disposed close to the first notches 451a formed at two corners of the first magnet 451. The charging electrode 471 having a positive (+) pole may be disposed around one of the first notches 451a and the charging electrode 472 having a negative (−) pole may be disposed around the other first notch 451a. As another example, the other pair of charging electrodes 473 and 474 may be disposed close to the second notches 453a formed at two corners of the second magnet 453. The charging electrode 474 having a positive (+) pole may be disposed around one of the second notches 453*a* and the charging electrode 473 having a negative (−) pole may be disposed around the other second notch 453*a*.

According to an embodiment, the charging electrodes 470 may be disposed to be exposed to the outside at corners of the seat 413. The pair of charging electrodes 471 and 472 disposed around the first notches 451*a* and the pair of charging electrodes 473 and 474 disposed around the second notches 453*a* may be symmetrically or asymmetrically arranged on the seat 413. For example, the charging electrode 471 at the upper end of the first magnet 451 may have a positive (+) pole and the charging electrode 472 at the lower end may have a negative (−) pole. The charging electrode 473 at the upper end of the second magnet 453 may be a negative (−) pole and the charging electrode 474 at the lower end may be a positive (+) pole. As another example, a first virtual line L1 connecting the positive (+) pole of the first notches 451*a* and the positive (+) pole of the second notches 453*a* and a second virtual line L2 connecting the negative (−) pole of the first notches 451*a* and the negative (−) pole of the second notches 453*a* may cross each other at the crossing point (O).

Figure 12A:
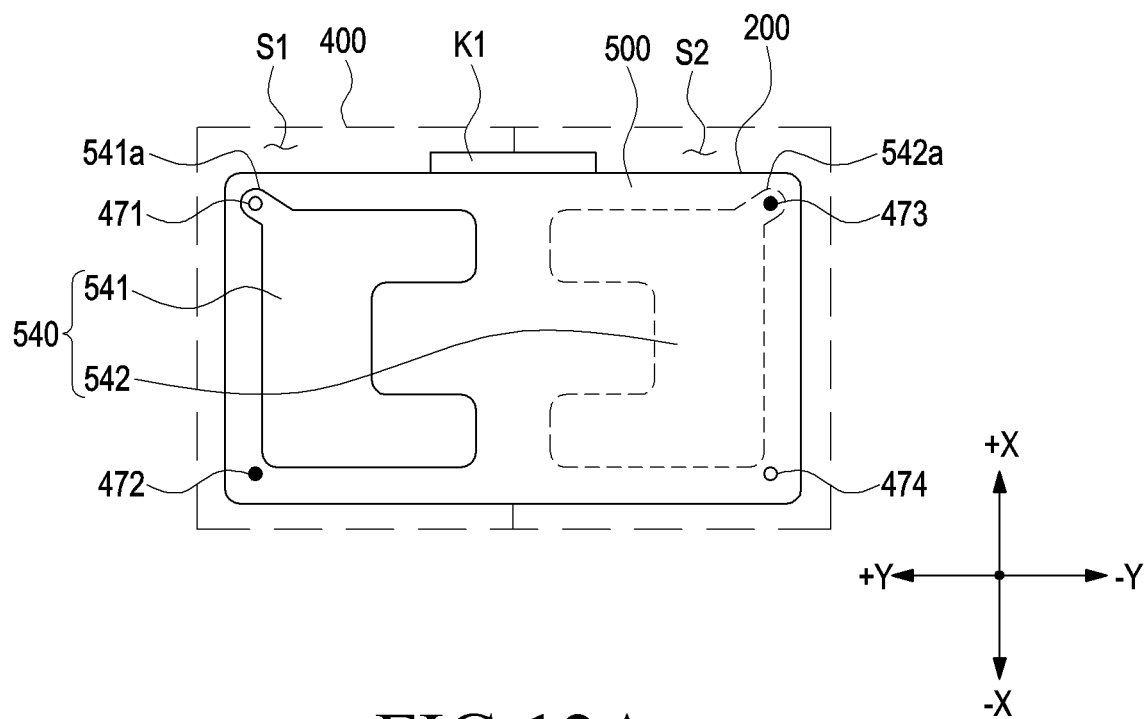
FIG. 12A is a view showing a self-arrangement relationship of a charging module system (the first electronic device 200 and the second electronic device 400) according to one of various embodiments.
Figure 12B:
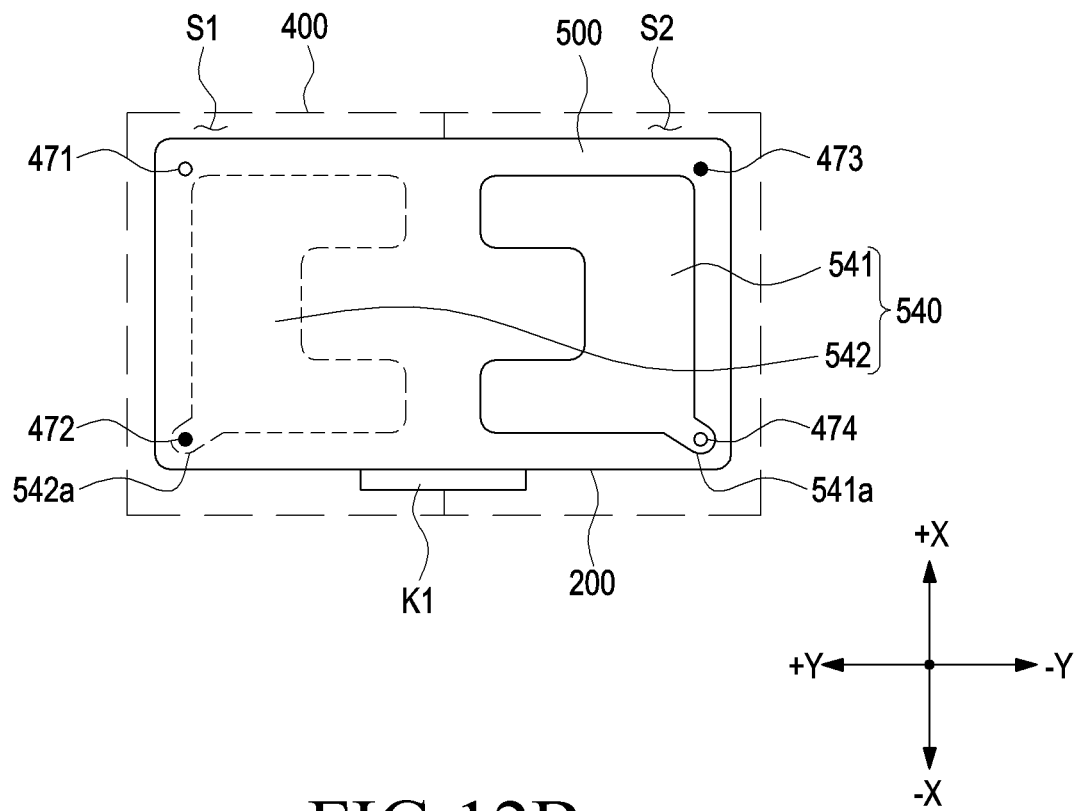
FIG. 12B is a view showing a self-alignment relationship of the second electronic device 400 with the first electronic device 200 of FIG. 12A turned 180 degrees.

FIG. 12A is a view showing a self-arrangement relationship of a charging module system (the first electronic device 200 and the second electronic device 400) according to one of various embodiments. FIG. 12B is a view showing a self-alignment relationship of the second electronic device 400 with the first electronic device 200 of FIG. 12A turned 180 degrees.

FIGS. 12A and 12B are, for helping understanding, projective views of the front surface of the first electronic device 200 when the first electronic device 200 is combined with the second electronic device 400. The structures of the first electronic device 200 and the second electronic device 400 of FIGS. 12A and 12B may be partially or entirely the same as the structures of the first electronic device 200 of FIGS. 2 to 8 and the second electronic device 400 of FIGS. 2, and 10 to 11.

Referring to FIGS. 2, 12A, and 12B, the charging module system may include a first electronic device 200 and a second electronic device 400, and the first electronic device 200 and the second electronic device 400 can be self-aligned. The first electronic device 200 includes a plurality of electrodes 540 and the electrodes 540 can be magnetically combined with a plurality of magnets (e.g., the magnets 450 of FIG. 11) of the second electronic device 400. For example, the same arrangement is shown in FIGS. 2 and 12A.

According to various embodiments, the electrodes 540 of the first electronic device 200 can be used to charge the battery 189 in the first electronic device 200 or measure biometric signs. According to an embodiment, the first electrode 541 and the second electrode 542 of the first electronic device 200 may be disposed to have different polarities. For example, when the first electrode 541 forms a positive (+) pole, the second electrode 542 may form a negative (−) pole.

According to an embodiment, the first electrode 541 may be disposed at the left side (e.g., in the +Y direction) from the center of the body 500 and the second electrode 542 may be disposed at the right side (e.g., in the −Y direction) from the center of the body 500. The first electrode 541 and the second electrode 542 may be spaced from each other to surround a biometric sensor (not shown) at the central area.

According to an embodiment, the first electrode 541 and the second electrode 542 of the first electronic device 200 may include a material having magnetism. The first electrode 541 and the second electrode 542 may include a substance having high conductivity, strong magnetic force, and high anticorrosion for self-alignment between the second electronic device 200 and a device. Further, they may be made of a substance that less influences the skin because they are supposed to come in direct contact with the skin of a user. For example the first electrode 541 and the second electrode 542 may be made of a material including ferritic stainless steel.

According to various embodiments, the electrodes 540 may have a notch structure having at least partial area protruding or recessed along the rear surface of the first electronic device 200. For example, the first electrode 541 may have a first notches 541*a* protruding from an upper outer corner. As another example, the second electrode 542 may have a second notch 542*a* protruding from an outer corner.

According to various embodiments, the second electronic device 400 may include a plurality of charging electrodes 471, 472, 473, and 474 and the charging electrodes 471, 472, 473, and 474 may form a crossing point with the first electrode 541 and the second electrode 542 of the first electronic device 200. The charging electrodes 471, 472, 473, and 474 may include two pairs of a positive (+) pole and a negative (−) pole, that is, a total of four electrodes. The pairs of a positive (+) pole and a negative (−) pole may be disposed in area adjacent to the notches (e.g., the first notches 541*a* and the second notches 542*a*) of the electrodes of the first electronic device 200 when the first electronic device 200 is seated on the seat 413 of the second electronic device 400.

According to an embodiment, the second electronic device 400 may include a first area S1 and a second area S2 extending from the first area. The pair of charging electrodes 471 and 472 may be disposed in the first area S1 and the pair of charging electrodes 473 and 474 may be disposed in the second area S2.

Self-alignment for charging the first electronic device 200 and the second electronic device 400 is described with reference to FIG. 12A. The first notch 541*a* of the first electrode 541 of the first electronic device 200 can form a crossing point with one of the charging electrodes of the second electronic device 400. For example, the first electrode 541 of the first electronic device 200 may be formed with the first notch 541*a* protruding upward (e.g., in the +X direction), to the left (e.g., in the +Y direction), or to the upper left and can form a crossing point with the positive (+) charging electrode 471 facing the area where the first notch 541*a* is disposed and disposed in the first area S1 of the second electronic device 400.

As another example, the second notch 542*a* of the second electrode 542 of the first electronic device 200 can form a crossing point with one of the charging electrodes of the second electronic device 400. For example, the second electrode 542 of the first electronic device 200 may be formed with the second notch 542*a* protruding upward (e.g., in the +X direction), to the right (e.g., in the −Y direction), or to the upper right and can form a crossing point with the negative (−) charging electrode 473 facing the area where the second notch 542*a* is disposed and disposed in the second area S2 of the second electronic device 400.

In the self-alignment state of FIG. 12A, other charging electrodes 472 and 474 of the second electronic device 400 may be disposed not to be in direct contact with the electrodes 540 of the first electronic device 200.

FIG. 12B shows a self-alignment state of the first electronic device 200 to be charged by the second electronic device 400 after the first electronic device 200 is turned 180 degrees from FIG. 12A. The first notch 541a of the first electrode 541 of the first electronic device 200 can form a crossing point with one of the charging electrodes of the second electronic device 400. For example, the first electrode 541 of the first electronic device 200 may be formed with the first notch 541a protruding downward (e.g., in the −X direction), to the right (e.g., in the −Y direction), or to the lower right and can form a crossing point with the positive (+) charging electrode 474 facing the area where the first notch 541a is disposed and disposed in the second area S2 of the second electronic device 400.

As another example, the second notch 542a of the second electrode 542 of the first electronic device 200 can form a crossing point with one of the charging electrodes of the second electronic device 400. For example, the second electrode 542 of the first electronic device 200 may be formed with the second notch 542a protruding downward (e.g., in the −X direction), to the left (e.g., in the +Y direction), or to the lower left and can form a crossing point with the negative (−) charging electrode 472 facing the area where the second notch 542a is disposed and disposed in the first area S1 of the second electronic device 400.

In the self-alignment state of FIG. 12B, other charging electrodes 471 and 473 of the second electronic device 400 may be disposed not to be in direct contact with the electrodes 540 of the first electronic device 200.

However, the notch structure of the first electronic device 200 is not limited thereto and can be changed in various shapes (e.g., a concave shape). The arrangement of the charging electrodes of the second electronic device 400 may depend on the shape and arrangement of the notch structure of the first electronic device 200.

According to various embodiments, by the arrangement of the electrodes of the first electronic device 200 having the arrangement and notch structure of the charging electrodes of the second electronic device 400, the first electronic device 200 can be charged at various positions and the battery can be charged. Further, the magnets in the second electronic device 400 (the magnets 450 of FIG. 11) can maintain a safe contact point in charging because they are magnetically combined with the electrodes of the first electronic device 200 made of a magnetic material.

Figure 13A:
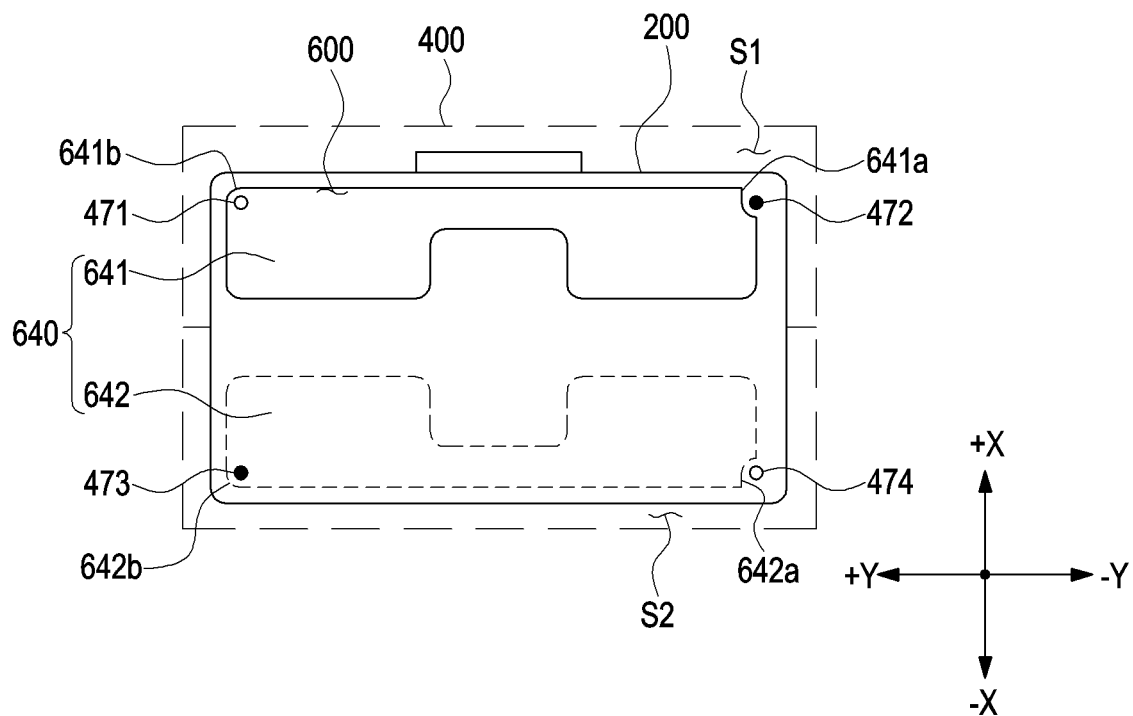
FIG. 13A is a view showing a self-arrangement relationship of a charging module system (the first electronic device 200 and the second electronic device 400) according to one of various embodiments.
Figure 13B:
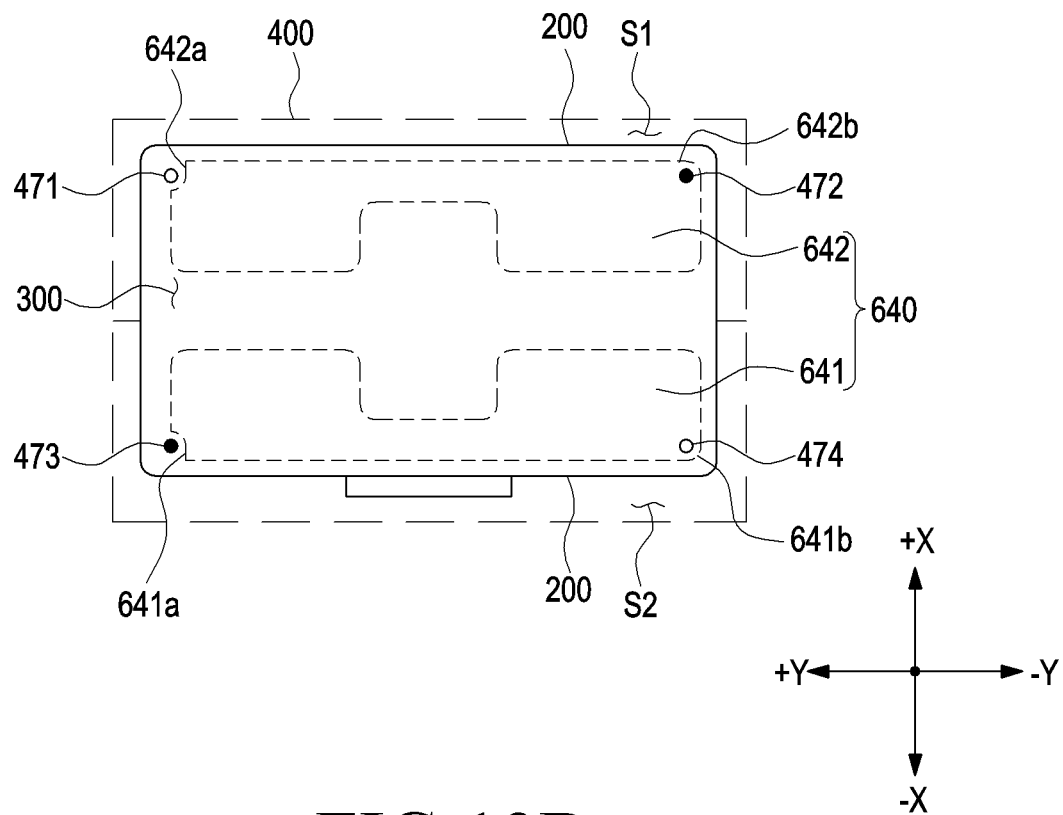
FIG. 13B is a view showing a self-alignment relationship of the second electronic device 400 with the first electronic device 200 of FIG. 13A turned 180 degrees.

FIG. 13A is a view showing a self-arrangement relationship of a charging module system (the first electronic device 200 and the second electronic device 400) according to one of various embodiments. FIG. 13B is a view showing a self-alignment relationship of the second electronic device 400 with the first electronic device 200 of FIG. 13A turned 180 degrees.

FIGS. 13A and 13B, for helping understanding, are projective views of the front surface of the first electronic device 200 when the first electronic device 200 is combined with the second electronic device 400. The structures of the first electronic device 200 and the second electronic device 400 of FIGS. 13A and 13B may be partially or entirely the same as the structures of the first electronic device 200 of FIGS. 2 to 8 and the second electronic device 400 of FIGS. 2, and 10 to 11.

Referring to FIGS. 2, 13A, and 13B, the charging module system may include a first electronic device 200 and a second electronic device 400, and the first electronic device 200 and the second electronic device 400 can be self-aligned. The first electronic device 200 includes a plurality of electrodes 640 and the electrodes 640 can be magnetically combined with a plurality of magnets (e.g., the magnets 450 of FIG. 11) of the second electronic device 400. For example, the same arrangement is shown in FIGS. 2 and 13B.

According to various embodiments, the electrodes 640 of the first electronic device 200 can be used to charge the battery in the first electronic device 200 (e.g., the battery 189 of FIG. 8) or measure biometric signs. According to an embodiment, the first electrode 641 and the second electrode 642 of the first electronic device 200 may be disposed to have different polarities. For example, when the first electrode 641 forms a positive (+) pole, the second electrode 642 may form a negative (−) pole.

According to an embodiment, the first electrode 641 may be disposed at the upper end (e.g., in the +X direction) from the center of the body 600 and the second electrode 642 may be disposed at the lower end (e.g., in the −X direction) from the center of the body 600. The first electrode 641 and the second electrode 642 may be spaced from each other to surround a biometric sensor (not shown) at the central area.

According to an embodiment, the first electrode 641 and the second electrode 642 of the first electronic device 200 may include a material having magnetism. The first electrode 641 and the second electrode 642 may include a substance having high conductivity, strong magnetic force, and high anticorrosion for self-alignment between the second electronic device 400 and a device. Further, they may be made of a substance that less influences the skin because they are supposed to come in direct contact with the skin of a user. For example the first electrode 641 and the second electrode 642 may be made of a material including ferritic stainless steel.

According to various embodiments, the electrodes 640 may have a notch structure having at least partial area protruding or recessed along the rear surface of the first electronic device 200. For example, the first electrode 641 may have a first notch 641a recessed at an upper outer corner. As another example, the second electrode 642 may have a second notch 642a recessed at an outer corner.

According to various embodiments, the second electronic device 400 may include a plurality of charging electrodes 471, 472, 473, and 474 and the charging electrodes 471, 472, 473, and 474 may form a crossing point with the first electrode 641 and the second electrode 642 of the first electronic device 200. The charging electrodes 471, 472, 473, and 474 may include two pairs of a positive (+) pole and a negative (−) pole, that is, a total of four electrodes. The pairs of a positive (+) pole and a negative (−) pole may be disposed close to the notches 641a and 642a or corners opposite to the notches of the first electronic device 200.

According to an embodiment, the second electronic device 400 may include a first area S1 and a second area S2 extending from the second area. The pair of charging electrodes 471 and 472 may be disposed in the first area S1 and the pair of charging electrodes 473 and 474 may be disposed in the second area S2.

Self-alignment for charging the first electronic device 200 and the second electronic device 400 is described with reference to FIG. 13A. The first notch 641a of the first electrode 641 of the first electronic device 200 may be disposed not to overlap one of the charging electrodes of the second electronic device 400. The first corner area 641b of the first electrode 641 disposed opposite the first notch 641a can form a crossing point with one of the charging electrodes of the second electronic device 400. For example, the first electrode 641 of the first electronic device 200 may be formed with the first corner area 641b positioned upward (e.g., in the +X direction), to the left (e.g., in the +Y direction), or to the upper left and can form a crossing point with the positive (+) charging electrode 471 facing the area where the first corner area 641*b* is disposed and disposed in the first area S1 of the second electronic device 400.

As another example, the second corner area 642*b* opposite to the second notch 642*a* of the second electrode 642 of the first electronic device 200 can form a crossing point with one of the charging electrodes of the second electronic device 400. For example, the second electrode 642 of the first electronic device 200 may be formed with the second corner area 642*b* positioned downward (e.g., in the −X direction), to the left (e.g., in the +Y direction), or to the lower left and can form a crossing point with the positive (−) charging electrode 473 facing the area where the second corner area 642*b* is disposed and disposed in the second area S2 of the second electronic device 400.

In the self-alignment state of FIG. 13A, other charging electrodes 472 and 474 of the second electronic device 400 may be disposed not to be in direct contact with the electrodes 640 of the first electronic device 200.

FIG. 13B shows a self-alignment state of the first electronic device 200 to be charged by the second electronic device 400 after the first electronic device 200 is turned 180 degrees from FIG. 13A. The first corner area 641*b* of the first electrode 641 of the first electronic device 200 can form a crossing point with one of the charging electrodes of the second electronic device 400. For example, the first electrode 641 of the first electronic device 200 may be formed with the first corner area 641*b* positioned downward (e.g., in the −X direction), to the right (e.g., in the −Y direction), or to the lower right and can form a crossing point with the positive (+) charging electrode 474 facing the area where the first corner area 641*b* is disposed and disposed in the second area S2 of the second electronic device 400.

As another example, the second corner area 642*b* of the second electrode 642 of the first electronic device 200 can form a crossing point with one of the charging electrodes of the second electronic device 400. For example, the second electrode 642 of the first electronic device 200 may be formed with the second corner area 642*b* positioned upward (e.g., in the +X direction), to the right (e.g., in the −Y direction), or to the upper right and can form a crossing point with the negative (−) charging electrode 473 facing the area where the second corner area 642*b* is disposed and disposed in the first area S1 of the second electronic device 400.

In the self-alignment state of FIG. 13B, other charging electrodes 471 and 473 of the second electronic device 400 may be disposed not to be in direct contact with the electrodes 640 of the first electronic device 200. However, the notch structure of the first electronic device 200 is not limited thereto and can be changed in various shapes (e.g., a convex shape). The arrangement of the charging electrodes of the second electronic device 400 may depend on the shape and arrangement of the notch structure of the first electronic device 200.

According to various embodiments, by the arrangement of the electrodes of the first electronic device 200 having the arrangement and notch structure of the charging electrodes of the second electronic device 400, the first electronic device 200 can be charged at various positions and the battery can be charged. Further, the magnets in the second electronic device 400 (the magnets 450 of FIG. 11) can maintain a safe contact point in charging because they are magnetically combined with the electrodes of the first electronic device 200 made of a magnetic material.

An electronic device according to various embodiments may include:

a housing 211 having a first surface facing a first direction and a second surface facing a second direction opposite to the first direction; a display device 213 at least partially exposed through the first surface to display information to the outside; a biometric sensor 330 disposed to be exposed in at least an area of the second surface and sensing biometric information of a user; a battery 189 disposed between the display device and the biometric sensor; and a plurality of electrodes 340 disposed adjacent to the at least an area of the second surface and formed to be exposed in at least another area of the second surface, wherein the plurality of electrodes may surround at least a portion of the biometric sensor and each of the plurality of electrodes may have a notch 341*a* or 342*a* protruding or recessed at least at one end.

According to various embodiments, the electrodes may include a first electrode 341 and a second electrode 342 opposite to each other with the biometric sensor therebetween and the notches are formed at least at a portion of each of outer edge areas of the first electrode and the second electrode.

According to various embodiments, the first electrode and the second electrode may have different polarities and form electrical contact points with an external electronic device (e.g., the second electronic device 400).

According to various embodiments, the first electrode may have a first notch 541*a* protruding from a corner area at one end of the first electrode facing the second electrode, the second electrode may have a second notch 542*a* protruding from a corner area at one end of the second electrode facing the first electrode, and the first notch and the second notch may be arranged in parallel with each other in the longitudinal direction of the housing.

According to various embodiments, the first notch may form a contact point with a first charging electrode 471 or 474 of the external electronic device and the second notch may form a contact point with a second charging electrode 472 or 473 of the external electronic device.

According to various embodiments, the first electrode may have a first notch 341*a* recessed in a corner area at one end of the first electrode facing the second electrode, the second electrode may have a second notch 342*a* recessed in a corner area at one end of the second electrode facing the first electrode, and the first notch and the second notch may be arranged in parallel with each other in the longitudinal direction of the housing.

According to various embodiments, the electrodes may include a material having magnetism and are magnetically coupled to magnets 540 of the external electronic device.

According to various embodiments, the electrodes may include ferrite stainless steel.

According to various embodiments, biometric sensor may include: at least one light source 331 emitting light; and a photodiode 333 spaced from the light source, receiving reflective light corresponding to the light emitted from the light source, and converting the received light into a current signal.

According to various embodiments, the electronic device may further include a processor 120 configured to obtain biometric information of a user using the biometric sensor or a communication module 190 of the electronic device, to determine at least one service related to the biometric information from a plurality of services that are supported by the electronic device, and to provide the determined service.

An electronic device according to various embodiments may include: a housing 410 having a seat 413 forming contact points with an external electronic device; at least one magnet 450 disposed in the housing to face the seat; and a plurality of charging electrodes 470 formed to be exposed to the seat from the housing and forming contact points with the external electronic device, wherein the electrodes may include a pair of first charging electrodes 471 and 472 having a positive (+) pole and a negative (−) pole and another pair of second charging electrodes 473 and 474 having a positive (+) pole and a negative (−) pole and disposed in parallel with a virtual line including the pair of first charging electrodes.

According to various embodiments, a first virtual line L1 in which the positive (+) pole of the first charging electrode and the positive (+) pole of the second charging electrode and a second virtual line L2 in which the negative (−) pole of the first charging electrode and the negative (−) pole of the second charging electrode may form a crossing point.

According to various embodiments, the magnets may include a first magnet 451 disposed in a first area of the seat and a second magnet 453 spaced from the first magnet and disposed on a second area extending from the first area of the seat. First ends of the first magnet and the second magnet facing the central area of the seat may be at least partially recessed, and both corner areas of second ends may be recessed in a notch structure.

According to various embodiments, the pair of first charging terminals 471 and 472 may be disposed in an area close to the notch 451a of the first magnet and the other pair of second charging terminals 473 and 474 may be disposed close to the notch 453a of the second magnet.

A charging module system includes a first electronic device 200 and a second electronic device 400 charging a battery 189 of the first electronic device according to various embodiments, wherein the first electronic device may include: a first housing 211; a biometric sensor disposed to be exposed on a surface of the first housing and sensing biometric information of a user; the battery 189 disposed in the first housing; and a plurality of electrodes 340 disposed opposite to each other with the biometric sensor therebetween and having an end with a protruding or recessed notch, the second electronic device may include: a second housing having a seat 413 where the first electronic device is seated; at least one magnet disposed in the second housing to face the electrodes of the first electronic device; and a plurality of charging electrodes 470 forming contact points with at least a portion of each of the notches of the electrodes of the first electronic device in the second housing, and the magnets of the second electronic device may have a shape corresponding to the electrodes of the first electronic device such that the surface of the first electronic device is self-aligned with the seat of the second electronic device.

According to various embodiments, the electrodes of the first electronic device may include a first electrode 341 and a second electrode 342 disposed opposite to each other with the biometric sensor therebetween, and the first electrode may be disposed in a first area (S1) of the second electronic device and the second electrode may be disposed in a second area (S2), which extends from the first area, of the second electronic device, or the first electrode may be disposed in the second area (S2) of the second electronic device and the second electrode may be disposed in the first area (S1) of the second electronic device.

According to various embodiments, a pair of first charging electrodes 471 and 472 having a positive (+) pole and a (−) negative pole may be disposed in the first area, which faces at least a portion of the first electrode, of the second electronic device, and another pair of second charging electrodes 473 and 474 having positive (+) pole and a negative (−) pole may be disposed in the second area, which faces at least a portion of the second electrode, of the second electronic device.

According to various embodiments, the electrodes of the first electronic device may include a material having magnetism and may form magnetic coupling, which allows for a plurality of arrangement relationships, with the magnets of the second electronic device.

According to various embodiments, a first notch protruding from the end of the first electrode of the first electronic device may form a contact point with one of the first charging electrodes having the positive (+) pole and the negative (−) pole disposed in the first area of the second electronic device, a second notch protruding from the end of the second electrode of the first electronic device forms a contact point with one of the second charging electrodes having the positive (+) pole and the negative (−) pole disposed in the second area of the second electronic device, and the polarity of the first charging electrode forming the contact point with the first electrode and the polarity of the second charging electrode forming the contact point with the second electrode may be different.

According to an embodiment, the notches include a first notch formed at an outer corner area of the first electrode and a second notch formed at an outer corner area of the second electrode, and the first notch and the second notch may have the same shape.

While the present disclosure has been shown and described with reference to certain embodiments thereof, it will be apparent to those skilled in the art that the camera lens module according to the present disclosure is not limited to these embodiments, and various changes in form and details may be made therein without departing from the spirit and scope of the present disclosure as defined by the appended claims.

What is claimed is:

1. A charging module system comprising an electronic device and a charging module for charging a battery of the electronic device, the electronic device comprising:
 a housing having a first surface facing a first direction and a second surface facing a second direction opposite to the first direction;
 a display device at least partially exposed through the first surface to display information to a outside;
 a biometric sensor disposed to be exposed in at least an area of the second surface and sensing biometric information of a user;
 the battery disposed between the display device and the biometric sensor; and
 a plurality of electrodes disposed adjacent to the at least an area of the second surface and formed to be exposed in at least another area of the second surface,
 wherein the plurality of electrodes surround at least a portion of the biometric sensor and each of the plurality of electrodes has a notch protruding or recessed at least at one end,
 wherein the plurality of electrodes include a first electrode and a second electrode opposite to each other with the biometric sensor therebetween, and
 wherein the first electrode has a first notch protruding from a corner area or recessed in a corner area at one end of the first electrode facing the second electrode, the second electrode has a second notch protruding from a corner area or recessed in a corner area at one end of the second electrode facing the first electrode, and the first notch and the second notch are arranged in parallel with each other in a longitudinal direction of the housing.

2. The charging module system of claim 1, wherein the notches are formed at least at a portion of each of outer edge areas of the first electrode and the second electrode.

3. The charging module system of claim 2, wherein the first electrode and the second electrode have different polarities and are configured to form electrical contact points with the charging module.

4. The charging module system of claim 1, wherein the first notch is configured to form a contact point with a first charging electrode of the charging module and the second notch is configured to form a contact point with a second charging electrode of the charging module.

5. The charging module system of claim 2, wherein the electrodes include a material having magnetism and are configured to be magnetically coupled to magnets of the charging module, and wherein the electrodes include ferrite stainless steel.

6. The charging module system of claim 3, wherein the biometric sensor includes: at least one light source emitting light; and a photodiode spaced from the light source, receiving reflective light corresponding to the light emitted from the light source, and converting the received reflective light into a current signal.

7. The charging module system of claim 3, further comprising a processor configured to obtain biometric information of a user using the biometric sensor or a communication module of the electronic device, to determine at least one service related to the biometric information from a plurality of services that are supported by the electronic device, and to provide the determined service.

8. The charging module system of claim 1, the charging module:
a housing having a seat configured to form contact points with the electronic device;
at least one magnet disposed in the housing to face the seat; and
a plurality of charging electrodes formed to be exposed to the seat from the housing and configured to form contact points with external electronic device,
wherein the electrodes includes a pair of first charging electrodes having a positive (+) pole and a negative (−) pole and another pair of second charging electrodes having a positive (+) pole and a negative (−) pole and disposed in parallel with a virtual line including the pair of first charging electrodes.

9. The charging module system of claim 8, wherein the pair of first charging electrodes and the other pair of second charging electrodes are arranged such that a first virtual line in which the positive (+) pole of the first charging electrode and the positive (+) pole of the second charging electrode and a second virtual line in which a negative (−) pole of the first charging electrode and the negative (−) pole of the second charging electrode form a crossing point.

10. The charging module system of claim 8, wherein the magnets include a first magnet disposed in a first area of the seat and a second magnet spaced from the first magnet and disposed on a second area extending from the first area of the seat, first ends of the first magnet and the second magnet facing a central area of the seat are at least partially recessed, and both corner areas of second ends are recessed in a notch structure, and wherein the pair of first charging terminals is disposed in an area adjacent to the notch of the first magnet and the other pair of second charging terminals is disposed adjacent to the notch of the second magnet.

11. A charging module system comprising a electronic device and a charging module charging a battery of the electronic device,
wherein the electronic device includes: a first housing; a biometric sensor disposed to be exposed on a surface of the first housing and sensing biometric information of a user; the battery disposed in the first housing; and a plurality of electrodes disposed opposite to each other with the biometric sensor therebetween and having an end with a protruding or recessed notch,
the charging module includes: a second housing having a seat where the first electronic device is seated; a plurality of magnets disposed in the second housing to face the electrodes of the first electronic device; and a plurality of charging electrodes configured to form contact points with at least a portion of each of the notches of the electrodes of the first electronic device in the second housing,
the magnets of the second electronic device have a shape corresponding to the electrodes of the first electronic device such that the surface of the first electronic device is self-aligned with the seat of the second electronic device,
wherein the plurality of electrode include a first electrode and a second electrode,
wherein the first electrode has a first notch protruding from a corner area or recessed in a corner area at one end of the first electrode facing the second electrode, the second electrode has a second notch protruding from a corner area or recessed in a corner area at one end of the second electrode facing the first electrode, and the first notch and the second notch are arranged in parallel with each other in a longitudinal direction of the housing.

12. The charging module system of claim 11, wherein the electrodes of the electronic device include a first electrode and a second electrode disposed opposite to each other with the biometric sensor therebetween, and
wherein the first electrode is disposed in a first area of the charging module and the second electrode disposed in a second area, which extends from the first area, of the charging module, or the first electrode is disposed in the second area of the charging module and the second electrode is disposed in the first area of the charging module.

13. The charging module system of claim 12, wherein the electrodes of the electronic device include a first electrode and a second electrode disposed opposite to each other with the biometric sensor therebetween,
wherein a pair of first charging electrodes having a positive (+) pole and a negative (−) pole is disposed in the first area, which faces at least a portion of the first electrode, of the charging module, and another pair of second charging electrodes having positive (+) pole and a negative (−) pole is disposed in the second area, which faces at least a portion of the second electrode, of the charging module,
wherein a first notch protruding from an end of the first electrode of the electronic device is configured to form a contact point with one of the first charging electrodes having the positive (+) pole and the negative (−) pole disposed in the first area of the charging module, a second notch protruding from an end of the second electrode of the electronic device is configured to form a contact point with one of the second charging electrodes having the positive (+) pole and the negative (−) pole disposed in the second area of the charging module, and a polarity of the first charging electrode configured to form the contact point with the first electrode and the polarity of the second charging electrode configured to form the contact point with the second electrode are different.

* * * * *